United States Patent
Berrang et al.

(10) Patent No.: US 6,358,281 B1
(45) Date of Patent: Mar. 19, 2002

(54) TOTALLY IMPLANTABLE COCHLEAR PROSTHESIS

(75) Inventors: Peter G. Berrang; Henry V. Bluger, both of Victoria; Stacey D. Jarvin, Brentwood Bay; Alan J. Lupin, Victoria, all of (CA)

(73) Assignee: Epic Biosonics Inc., Victoria (CA)

( * ) Notice: Subject to any disclaimer, the term of this patent is extended or adjusted under 35 U.S.C. 154(b) by 0 days.

(21) Appl. No.: 09/450,025

(22) Filed: Nov. 29, 1999

(51) Int. Cl.$^7$ .................................................. A61F 2/18

(52) U.S. Cl. .............................. 623/10; 607/57; 600/25

(58) Field of Search ............................... 623/10; 607/57, 607/56, 137; 600/25; 181/126–131; 381/68–692

(56) References Cited

U.S. PATENT DOCUMENTS

| | | | |
|---|---|---|---|
| 4,357,497 A | | 11/1982 | Hochmair et al. |
| 4,419,995 A | | 12/1983 | Hochmair et al. |
| 4,441,210 A | | 4/1984 | Hochmair et al. |
| 4,532,930 A | | 8/1985 | Crosby et al. |
| 5,070,535 A | | 12/1991 | Hochmair et al. |
| 5,279,292 A | | 1/1994 | Baumann et al. |
| 5,282,858 A | * | 2/1994 | Bisch et al. .................... 623/10 |
| 5,578,084 A | * | 11/1996 | Kuzma et al. ................. 623/10 |
| 5,645,585 A | * | 7/1997 | Kuzma ........................... 623/10 |
| 5,788,711 A | * | 8/1998 | Lehner et al. ............... 606/130 |
| 5,876,425 A | | 3/1999 | Gord et al. |
| 5,891,183 A | | 4/1999 | Zierhofer |
| 5,906,635 A | * | 5/1999 | Maniglia ........................ 607/57 |
| 5,984,859 A | * | 11/1999 | Lesinski ........................ 623/10 |
| 6,010,532 A | * | 1/2000 | Kroll et al. ..................... 623/10 |

OTHER PUBLICATIONS

G.M. Clark et al., "Cochlear Prostheses", Churchill Lvingstone, New York, 1990.

T.J. Balkany, "The Cochlear Implant", The Otolaryngologic Clinics of North America, vol. 19/No. 2, May 1986, W.B. Saunders Company, Philadelphia.

A.J. Maniglia et al., "The Middle Ear Bioelectronic Microphone for a Totally Implantable Cochlear hearing Device for Profound and Total Hearing Loss", The American Journal of Otology, vol. 20, No. 5, 1999, p. 602–611.

S.J. Rebscher, "Cochlear Implant Design and Construction", Chapter 4, Cochlear Implants, London, 1985, p. 74–123.

(List continued on next page.)

Primary Examiner—David H. Willse
Assistant Examiner—Suzette J. Jackson
(74) Attorney, Agent, or Firm—Paul R. Smith

(57) ABSTRACT

A totally implantable cochlear prosthesis is presented. Said prosthesis is designed to function for hours or days without any external components. An externally-activated subcutaneous pressure switch enables the user to adjust the perceived volume by pressing against the skin with a finger. A similar second pressure switch provides a safety "off/on" feature. A pliable bridge connecting two hermetically sealed housing sections, and corrugated conductor lines, provide for future dimensional changes due to head growth. A titanium encapsulated microphone is positioned underneath the skin in the posterior wall of the external auditory canal. A modiolus-hugging electrode array is inserted into one of the cochlea scala. Periodic charging of the implanted battery (contained within one of the housing sections) is required, such charging accomplished via an external mechanically held head-mounted device containing an external coil, said external coil inductively coupling electrical power to an implanted receiving coil. The external and implanted coils can also be used as a communication link to program the implanted electronics.

28 Claims, 15 Drawing Sheets

OTHER PUBLICATIONS

M. Soma, "Design and Fabrication of an Implantable Multichannel Neural Stimulator", Technical Report No. G908–1, National Institutes of Health Contract No. N01–NS–5–2306, Jun. 1980.

C.M. Zierhofer et al., "High–Efficiency Coupling–Insensitive Transcutaneous Power and Data Transmission Via an Inductive Link", IEEE Transactions on Bio–Medical Engineering, vol. 37, No. 7, Jul. 1990, p. 716–722.

B.P. Weber et al., "Magnetic Resonance Imaging Compatibility Testing of the Clarion 1.2 Cochlear Implant", The American Journal of Otology, vol. 19, No. 5, 1998, p. 584–590.

A.F. Von Recum, "Handbook of Biomaterials Evaluation", Macmillan Publishing Company, New York, 1986.

Shi–Ang Xu et al., "Evaluation of Expandable Leadwires for Pediatric Cochlear Implants", The American Journal of Otology, vol. 14, No. 2, Mar. 1993.

G.K. Maclean, "Preliminary Evaluation of Rechargeable Lithium–ion Cells for an Implantable Battery Pack", Journal of Power Sources 56 (1995) 69–74.

J. Bates et al., "Thin Film Rechargeable Lithium Batteries for Implantable Devices", ASAIO Journal, vol. 43, No. 5, 1997.

A.E. Deddens et al., "Totally Implantable Hearing Aids: the Effects of Skin Thickness on Microphone Function", American Journal of Otolaryngology, 11: 1–4, 1990.

J.A. Feigin et al., "The Effect of Reference Microphone Placement on Sound Pressure Levels at an Ear Level Hearing Aid Microphone", Ear and Hearing, vol. 11, No. 5, The Williams & Wilkins Co., 1990.

* cited by examiner

TOTALLY IMPLANTABLE COCHLEAR PROSTHESIS

FIELD OF THE INVENTION

This invention relates generally to human hearing, and more specifically to the design and surgical insertion and positioning of a totally implantable cochlear prosthesis.

BACKGROUND OF THE INVENTION

Human deafness results from numerous sources including trauma, ear infections, congenital factors, ototoxic effects of some antibiotics, and from diseases such as meningitis. Sensorineural damage (damage to the hair cells in the cochlea) is the largest single form of hearing loss. In a healthy ear these hair cells convert acoustic signals in the inner ear to electrical signals that can be interpreted by the brain as sound. It is estimated that over 7% of the U.S. population is affected by sensorineural deafness, and one in a thousand infants is born totally deaf. Extrapolating these percentage figures, it is estimated that there are more than 30 million people in the world who are profoundly deaf.

Currently available cochlear prostheses generally use an internal part containing an electrode array for insertion into the cochlea, and at least some electronics in a sealed subcutaneous package. Information is inductively transmitted through the skin via a head-mounted (magnetically held) device to the subcutaneous package, which package is designed to receive and process coded information for further transmission to the electrode array. The battery and a major part of the acoustic signal-processing electronics are housed in an externally worn device. These designs are not aesthetically pleasing, nor practical for sleeping or for other activities such as diving, swimming or other physical activities. Besides the inconvenience of said designs, there is a social stigma, especially for children, in wearing a head-mounted device, connected to an externally visible apparatus. Additionally, the length of surgery and the surgical complexity of implanting current commercial cochlear prostheses is significant, especially for very young and for very old persons. Said implant procedure involves exposure of the mastoid cortex and external auditory canal of the implanted ear via elevation of a postauricular skin flap, generally requiring 2–4 hours where the patient is totally anesthetized, with the inherent medical risks of total anesthetic. Finally, the cost of said cochlear prostheses is high, limiting the availability of this technology mostly to the wealthy industrialized countries.

In spite of the surgical risks, complexity and device costs, currently available cochlear prostheses do provide a major improvement over the alternative—total deafness. However, there are still great differences in hearing percepts amongst implanted patients. Some patients after implantation are able to use the telephone, while others can only perceive environmental sounds.

Such cochlear prostheses are commercially available from a number of companies worldwide, for example, from Cochlear Limited, Sydney, Australia; Advanced Bionics Corporation, Sylmar, Calif., U.S.A.; Med-El Medical Electronics, Innsbruck, Austria; PHILIPS-Antwerp Bionic Systems N.V./S.A., Edegem, Belgium; and MXM Medical Technologies, Vallauris, France. A comprehensive introduction to the development of cochlear implants is given in, for example, "Cochlear Prostheses," edited by G. M. Clark, Y. C. Tong and J. F. Patrick, distributed in the U.S.A. by Churchill Livingstone Inc., New York, N.Y. (ISBN 0-443-03582-2), and in "The Cochlear Implant," (ISSN 0030-6665) by T. J. Balkany, editor of The Otolaryngologic Clinics of North America, Vol. 19, No. 2, May, 1986. Some of the early cochlear implant work is also described in, for example, U.S. Pat. 4,357,497; 4,419,995 and 4,532,930.

Although a commercial totally implanted cochlear prosthesis does not yet exist, A. J. Maniglia in U.S. Pat. 5,906,635 and A. J. Maniglia, et. al. in "The Middle Ear Bioelectronic Microphone for a Totally Implantable Cochlear Hearing Device for Profound and Total Hearing Loss", in The American J. of Otology, 20:602–611, 1999, describe a possible design for a totally implanted device. Their proposed device uses a permanent magnet attached to the malleus which movement is detected by a nearby coil so as to detect vibrations of the ear drum. Said design uses a relatively complex arrangement of hermetically sealed packages, rods and brackets. A separate external RF linked unit is used to control the volume and on/off functions. The Maniglia prior art has a number of shortcomings namely: (a) said design is not MRI compatible, (b) a large excavation is required in the mastoid cavity to anchor and position said device, (c) mounting a magnet directly onto the ossicular chain can reduce the blood supply, creating the danger of future necrosis of the bone, (d) the device is not suitable for use in newborns, (e) there is no manual panic safety off switch, and (f) there is no allowance for future head growth between the various permanently anchored mounting brackets.

A totally implantable cochlear prosthesis of the present invention is designed to address the limitations of the prior art and to: (a) significantly improve the aesthetics and practical problems of coping with the relatively bulky external components of conventional cochlear prostheses, (b) allow the user to hear more naturally via the auditory canal (ear canal) and (c) enable versatile speech processing algorithms to be used to stimulate the auditory nerve cells for improved speech perception. Additionally, the implant is designed to reduce the surgical complexity and time needed by the surgeon for device implantation.

SUMMARY OF THE INVENTION

In one of its aspects, the invention comprises two parts, namely:

1. An implanted part, and
2. An external part

The implanted part itself embodies further aspects of the invention. The implanted part comprises four principal components:

(a) a housing
(b) a coil
(c) a microphone, and
(d) an electrode array

1. The Implanted Part

The implanted part is a stand-alone fully functional cochlear prosthesis, such functionality only limited by the capacity of the battery, or other storage device, contained within the implant housing. Said implanted part is comprised of a housing, coil, microphone and electrode array, where all components in contact with body tissues are biocompatible, and all non-biocompatible materials are substantially hermetically sealed with biocompatible materials. Such hermetic sealing is required to prevent ingress of biological fluids into the enclosure, creating device malfunction, and/or to prevent leakage of non-compatible material into the surrounding biological tissues. Medical devices such as conventional cochlear prostheses or pacemakers commonly use titanium enclosures (or ceramic enclosures with metal sputtered bonding surfaces) which are hermetically sealed using laser welding. For a brief review of sealing concepts, see for example, S. J. Rebscher's article in Chapter 4 (Cochlear Implant Design and Construction), published in Cochlear Implants, ed. Roger F. Gray, Croon Helm Ltd., London, 1985.

The preferred embodiment is to position the housing and coil substantially against the skull, posterior to the pinna, with the electrode array entering the middle ear via a mastoid cavity and facial recess approach, using either a modified version of a cochleostomy in conjunction with a transcanal approach. Such surgical cavity also allows for convenient positioning of the microphone underneath the skin in the posterior wall of the external auditory canal.

The connections from the microphone and electrode array to the housing are comprised of, preferably, platinum and/or gold wires formed lithographically, said wires encapsulated in a bioinert polymer, such as the fluorocarbon polymer FEP. Said connections are "corrugated" to enable the connections to expand with minimum stress during surgical handling, skull growth, and any post surgical movement of the implanted components.

(a) The Housing

The housing, which contains the wiring interconnections, electronics, battery, means for setting volume and safety "off/on", and, in an alternate embodiment, magnets, is positioned substantially against the skull behind the outer ear (or pinna) where said housing can be conveniently sutured to the overlying tissue or attached to the underlying bone with sutures, or titanium screws. Said housing comprises two sections, each section having a relatively thin and rounded profile at the edges, where such sections are joined by a pliable (or bendable) bridge to allow the surgeon to bend said bridge so as to better fit the two housing sections to the curved surface of the skull.

The key components within the housing sections are mounted on an insulated substrate (containing hermetically sealed electrical lead-throughs), where the substrate is comprised of ceramic or glass or a combination thereof, but preferentially ceramic, where the substrate is further bonded to an underlying cable, preferably a ribbon type cable, containing wires, where said ribbon cable is preferably comprised of a bioinert polymer film encapsulating lithographically formed wires. Openings within the polymer film allow electrical connections to be made from said conducting wires to the overlying ceramic substrate lead-throughs. The polymer film is then further bonded to an underlying gold foil substrate. Since some of said components may be comprised of non-biocompatible materials, they require complete hermetic or hermetic like sealing on all surfaces. The preferred embodiment to achieve such all surface sealing is to use a medical grade epoxy to cover said components (mounted onto the ceramic substrate), where said epoxy also provides shape to the overall housing. Alternately, any conformable potting material, such as a bioinert polymer, can be used as an encapsulant material to cover said components. Since epoxy, or other, encapsulation (over the ceramic substrate) does not provide a true hermetic or hermetic like seal, said encapsulant surface is coated first, preferably, with a thin coating of vacuum deposited gold, or alternately, with an electroless gold deposition, where such a first coating of gold is subsequently thickened by an electro deposition of gold. Alternate embodiments include coating the electro deposited gold layer with titanium (or platinum), and/or with medical grade silicone. The same gold coating processes are also used to provide a gold seal between the bridge connecting the two housing sections, and the point at which the connectors from the microphone and electrode array enter the housing bridge.

Since the encapsulant substantially covers the components within the two housing sections, in one embodiment, hollow beads or microcontainers containing, for example, helium gas and or other leak detection gases, are positioned within the encapsulant to act as a leak detection gas using standard quadrupole mass spectrometry, such gas leak detection system acting to verify the extent of the housing hermeticity.

In further embodiments, a laser, ultrasonic or electric welded titanium, ceramic (or a hybrid of both) enclosure may be used as the housing. For any ceramics used, these would need to be coated with titanium at any locations required for subsequent welding.

The various electronics within the housing should draw minimal power, and occupy a relatively small volume. The preferred embodiment is to use a custom designed low power hybrid analog-digital ASIC microchip for processing signals from the microphone and for controlling the current pulses to the cochlear electrodes. Alternately, a more conventional DSP based electronics design can be used, such design using a combination of standard and/or custom circuits. However, such a DSP design generally requires more power and space. The key advantages of using an analog-digital microchip are that such a device has very low power requirements, occupies a very small volume, and is inherently more reliable than using numerous discrete electronic components.

For the preferred embodiment, a thin film secondary (rechargeable) lithium battery is located in one housing section. Preferably, such a battery should have high charge density, be substantially rechargeable over tens of thousands of charge/discharge cycles, and use a safe solid state electrolyte. Alternately, a rechargeable nickel metal hydride battery can be used, although such a battery has a relatively low charge/discharge cycle capability, thus requiring surgical replacement every few years. A further alternate embodiment is to use a simple capacitor for short term storage of electrical power, in lieu of a battery storage system, where such a design would be used in conjunction with an externally-worn head mounted inductively coupled power input device worn continuously by the implantee.

Control of power and volume to the implanted part can be accomplished in a myriad of conventional ways, such as an RF link, IR light pulses, or acoustic signals through the skin. However, the invention uses a mechanical method to operate a panic "off/on" control, and an overall "volume" control. A panic shut off of the electronics is preferred in the event of device failure which could send excessive current to the cochlea electrodes, damaging the neural processes therein. However, such a safety shut off is preferably independent of the control electronics and should be capable of being quickly implemented by the user, in any setting. Ideally, the panic "off/on" control does not need a sophisticated external device to activate said control. According to the invention, a panic "off/on" control incorporates a pressure switch (located within a housing section), preferably a piezoceramic or piezocrystal disc (or a bimorph) mounted on a thin metal diaphragm, where such diaphragm can be slightly bent by the user by simply pushing (ie. with a finger) against the skin behind the pinna, thus producing an electrical signal from the piezoceramic that can be used by the electronics to control the panic "off/on" switch. In an alternate embodiment, a piezoelectric film such as PVDF (polyvinylidene fluoride), or copolymers of PVDF, produced by Measurement Specialties, Inc. of Valley Forge, Pa. can be used, where said piezo film is held in a "drum-like" configuration. The surface of said film can be (indirectly) pressed, through the skin surface, by the user by simply pushing (ie. with a finger) against the skin behind the pinna. Such pressure slightly deflects the PVDF film membrane inducing sufficient current and voltage to the control electronics to disengage power to the electrodes in the cochlea. In an alternate embodiment a mechanically-actuated electrical switch for the panic "off/on" switch can also be used in place of a piezo type device. To assist the implantee with a tactile sense as to when a contact is made, a snap dome can be used in conjunction with the piezo type panic "off/on" switches, or the mechanically-actuated electrical switches. Also, the use of a snap dome provides for a better signal since the operation of the piezo type or mechanical type switch will be suddenly activated when the pressure on the snap dome reaches a certain value.

In yet a further embodiment, a second panic "off/on" control using a magnetic reed switch is located in a housing section, which switch is normally in the closed mode, except when exposed to a magnetic field, such field opening the reed switch, disengaging power to the electrode array. The user can simply hold a magnet against the skin substantially over said switch thereby inducing a magnetic field through the skin to activate the reed switch. Removing the external magnet would close the reed switch thereby activating the implanted prosthesis again.

A piezoceramic or piezocrystal disc (or bimorph) or, alternately, a PVDF type piezo film can also be used as a "volume" control switch, similar to the panic "off/on" control design, to enable the user to adjust the volume "up" or volume "down" so as to achieve the preferred sound level. Said "volume" control can be mounted within one of the housing sections, and activated through the skin surface by the user pushing (ie. with a finger) against the skin behind the pinna, such pressure producing sufficient current and voltage from the piezoceramic, piezocrystal or piezo film material to activate the appropriate microelectronic circuits. In an alternate embodiment a mechanically-actuated electrical switch can also be used in place of a piezo type device. To assist the implantee with a tactile sense as to when a contact is made, a snap dome can be used in conjunction with the piezo type panic "off/on" switches, or the mechanically-actuated electrical switches. Also, the use of a snap dome provides for a better signal since the operation of the piezo type or mechanical type switch will be suddenly activated when the pressure on the snap dome reaches a certain value.

(b) The Coil

An external coil and an implanted coil are used to inductively couple electrical power and data through the skin surface. This technology is well established: see for example, Chapter 7 of "Design and Fabrication of an Implantable Multichannel Neural Stimulator", by M. Soma, June 1980, Technical Report No. G908-1, National Institute of Health Contract No. N01-NS-5-2306; and "High-Efficiency Coupling-Insensitive Transcutaneous Power and Data Transmission Via an Inductive Link", C. M. Zierhofer, et. al., IEEE Transactions on Biomedical Engineering, vol. 37, no. 7, July 1990. Also, a myriad of patents addressing various methods for improving or modifying such inductive links have issued, see for example, U.S. Pat. Nos. 4,441,210; 5,070,535; 5,279,292; 5,876,425; and 5,891,183. Unfortunately, the inductively coupled signal is attenuated by metallic layers present over the coil or metallic parts (such as magnets) contained within the coil perimeter. Such attenuation is also a function of the frequency of the transmitted signal.

The preferred embodiment of the present invention uses two RF coupling coils which are not RF shielded, and locates the implanted coil outside the housing. The coil comprises a number of turns of a biocompatible metal, such as platinum, titanium, gold, tantalum, iridium, rhodium, or rhenium, or any combination thereof, encapsulated in a bioinert polymer carrier, preferably a polyfluorocarbon such as FEP. The coil can be fabricated using discrete wires, or preferably, using lithographed tracks. An added advantage of such a design is that the coil has a very thin profile, and is flexible, thus fitting easily to the curved skull surface. Also, the center area within the coil may be made substantially "open", such a design minimizing the surface area separating the skull and overlying skin. A further advantage of the invention is the absence of a subcutaneous magnet or magnetizable material, within the coil perimeter, or housing, thus enabling an implantee to have an MRI scan without explantation of part or all of the implanted prosthesis. Commercial cochlear prostheses containing implanted magnets can restrict the user from having an MRI scan (see for example, B. P. Weber, et. al., vol. 19, no. 5, pages 584–590, 1998, American J. of Otology).

Also, it is advantageous to include a method for identifying the model, date or serial number of the implant, post surgery, using a non-invasive technique such as X-ray, CT scan or other medical imaging methods. Such identification can be conveniently accomplished by locating numbers, letters, marks or other identifying symbols substantially on the inside or outside perimeter of the coil, where such identifying markings can be conveniently fabricated lithographically in, for example, platinum or gold within a polymer film, such film also containing the coil wire, or lithographed coil tracks. Alternately, said markings can also be located anywhere on the implanted part where such markings would be identifiable using medical imaging methods.

(c) The Microphone

In the preferred embodiment a small microphone is encapsulated in a bioinert material such as titanium, gold, platinum, iridium, tantalum, rhodium or rhenium, or a polymer, such as a polyfluorocarbon, or any combination thereof, but preferably a titanium housing, said encapsulated microphone anchored in the posterior wall of the external auditory canal. A small mastoidectomy cavity is created surgically and the skin of the posterior wall of the external auditory canal is elevated. The bony wall between the mastoid cavity and the external auditory canal is thinned down to match the dimensions of the encapsulated microphone. A hole is created in the posterior wall of the external auditory canal about half way between the tympanic ring and the meatus of the external canal. This hole is also made substantially to the dimensions of the encapsulated microphone, using an appropriately sized drill bit and a custom designed hand tool. The thin diaphragm, preferably titanium, covering the sound input part of the encapsulated microphone, is fitted so as to lie underneath the skin of the posterior wall of the external auditory canal. In an alternate embodiment, a protective cap is placed over the titanium diaphragm during handling to protect it from damage.

Sound entering the user's auditory canal, will be received by the microphone, with the acoustic signal converted to an electrical signal within the microphone, where the electrical signal is then sent to the electronics within the housing for signal processing. One or more of numerous signal processing strategies may then be used to send electrical current pulses to the electrode array for stimulating the auditory nerve fibers, such stimulation being perceived by the user as sound.

(d) Electrode Array

The description of the preferred embodiment of the electrode array is disclosed in U.S. patent application Ser. No. 09/376,918 which is incorporated herein by reference. However, any compatible electrode array could be attached to the housing.

2. The External Part

An external part is required from time to time to recharge the battery, or other storage device, contained within the implanted housing. Such recharging of the internal battery (or other storage device) can be conveniently accomplished by, for example, using an external part to inductively couple power through the skin surface to an implanted receiving coil contained within, or preferably outside of, the implanted housing whereby the electrical power received by the implanted coil is used to charge the implanted battery (or storage device). Such external part is preferably held to the head either by mechanical means or, alternately, by magnetic means. For the preferred embodiment, the external coil is mounted behind the pinna on the arm of the frame of eye glasses, such that the external coil substantially overlays the implanted coil. Power to the external coil can be provided by including a battery (which itself may be rechargeable) and control electronics attached to the eye glass frame, or via a wire to a body-mounted power source. Alternately, the external coil can be mounted behind the pinna using a standard "BTE" device (like a behind-the-ear hearing aid package) to anchor and position the external coil substantially over the implanted coil. Power to the external coil can be provided by mounting the battery and control electronics directly on the BTE device, or via a wire to a body mounted power source.

A further embodiment is to use an arrangement of external and implanted magnetic fields to both hold the external part against the head and to also rotationally align said external device, such rotational alignment enabling the external coil and implanted coils to be substantially coaxial to achieve optimum inductive coupling. Such rotational alignment between the external and internal magnetic fields is necessary since the magnets and coil in each of the external and implanted parts are separated (ie. the magnet is not placed within the coil perimeter).

A yet further embodiment is to use a conventional method of alignment whereby opposing external and implanted magnets (which are each coaxial with and contained within the coil perimeter) are used such that the external part will be magnetically held against the head to position the external coil substantially over the implanted coil.

The external and implanted coils can also be used to transmit and or receive coded information to/from the electronics in the implanted housing to control or monitor electrical parameters in said housing.

In a yet later embodiment, the external part can be connected to a computer such that data can be generated by said computer to transmit electronic signals to the implanted part to change the parameters within the electronics of the implanted part.

For the embodiments where the external part contains a battery, such battery may be a secondary (or rechargeable) battery, or, in an alternate embodiment, a primary battery that is discarded after usage.

BRIEF DESCRIPTION OF DRAWINGS

The preferred and alternative embodiments of the invention will be described by reference to the accompanying drawings, where anterior is towards the front, posterior is towards the rear, superior is up, inferior is downwards, and lateral is away from the median of the head.

For drawings that show the right side of the head, such drawing would be equally applicable for the left side of the head. All references for the left side are applicable for the right side, and visa versa.

DESCRIPTION OF THE PREFERRED AND ALTERNATE EMBODIMENTS AND BEST MODE

Figure 1:
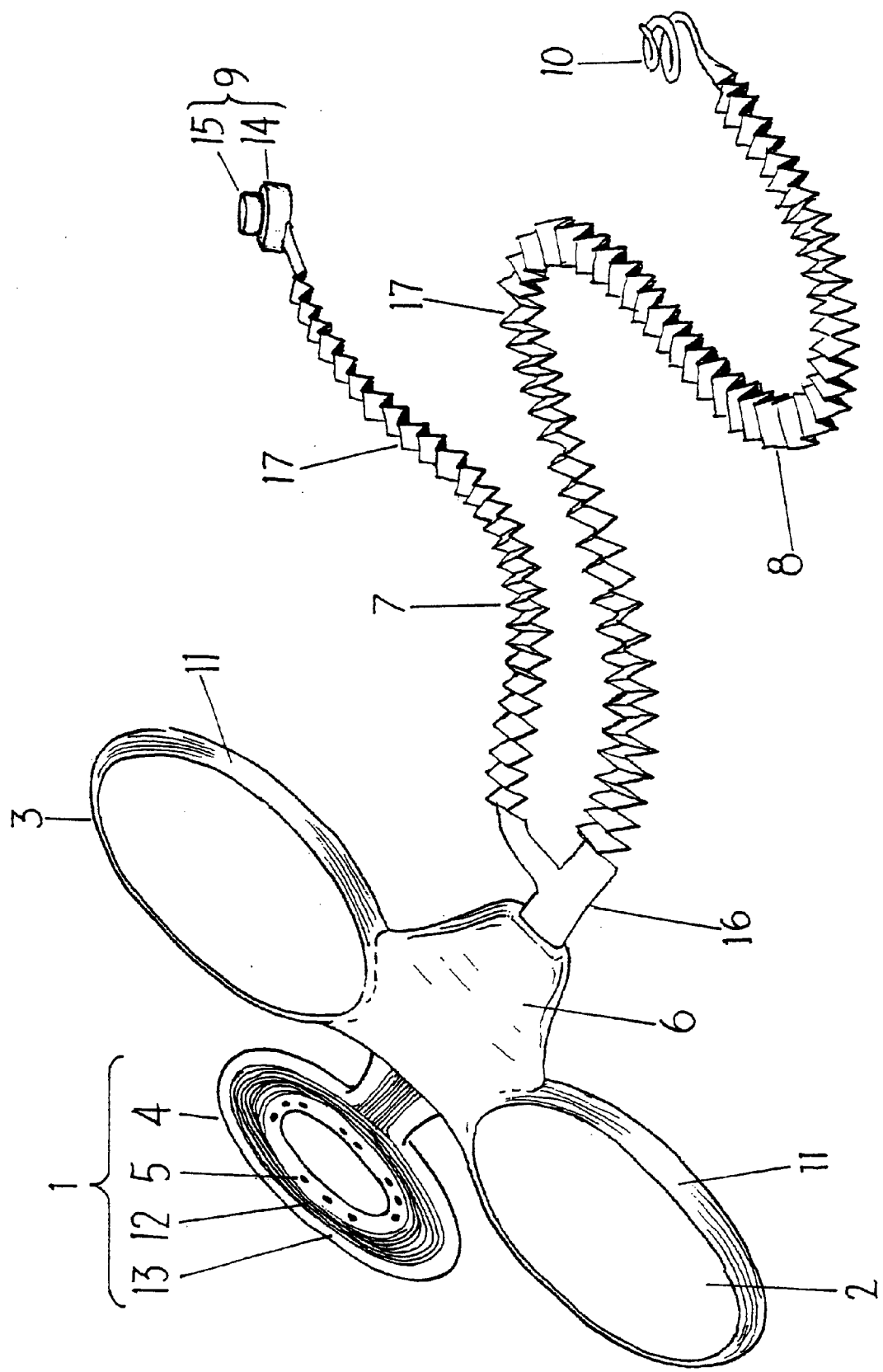
FIG. 1 shows an isometric view of the preferred embodiment of the implanted part of the invention, showing the two housing sections, the coil, the microphone, the electrode array, and the connector lines, including the corrugations thereon, joining the microphone and electrode array to the pliable bridge between the housing sections.

FIG. 1 shows an isometric view of the preferred embodiment of the implanted part 1 of the invention. Said invention 1 is comprised of two housing sections 2 and 3, a coil 4, identification markers 5, a pliable (or bendable) bridge 6, corrugated connections 7 and 8, a microphone 9 and an electrode array 10. All materials in contact with tissues are preferably comprised of biomaterials such as gold, platinum, palladium, tantalum, rhenium, rhodium, titanium, medical grade silicone and bioinert polymers, such as the polyfluorocarbons, and specifically the fluoropolymer FEP. A review of biomaterials can be found in a book edited by A. F. von Recum titled "Handbook of Biomaterials Evaluation", ISBN 0-02-42-423110-X.

The preferred embodiment of the housing is comprised of two sections 2 and 3 connected by bridge structure 6 containing a pliable metal (such as gold or platinum) so as to substantially allow a bent shape on insertion, such bendable bridge 6 allowing the surgeon to better fit the housing sections 2 and 3 to the curvature of the implantee's skull, especially for the small skulls of infants and children, and to allow for future skull growth. The housing sections 2 and 3 and bridge structure 6 are preferentially coated with gold, and, in a further embodiment, further coated with titanium, platinum, medical grade silicone, or any combination thereof.

For surgical reasons, the housing sections 2 and 3 should be as thin as possible to minimize the "bump" on the skin overlaying the housing sections 2 and 3, and to minimize the likelihood of trauma. In infants such skin thickness varies from about 1 mm to 1.5 mm, and in adults from 3 mm to 6 mm. Relatively thin housing sections 2 and 3 allow the surgeon to lay said sections substantially against the skull bone, generally without the need to excavate underlying bone. For the preferred embodiment, the housing thickness of sections 2 and 3 is about 2.0 to 2.9 mm with the edges 11 of said housing sections 2 and 3 rounded to minimize the entrainment of fluid or air pockets (to minimize creating a nidus for infection), and to prevent gradual erosion of the device through the skin. In an alternate embodiment, the housing sections are thicker than 2.9 mm, namely about 3 mm to 5 mm, in which case such thickness generally requires some excavation of skull bone to sink the housing into said bone, thus lowering the housing profile to protect the implantee from trauma.

Sections 2 and 3 each have a diameter of about 10 mm to 40 mm, preferably about 20 mm to 25 mm., such dimension containing all required components and providing the least disruption of tissue planes.

The coil 4 is comprised of a plurality of turns of biocompatible wire 12, or preferably, wire formed lithographically via electro or electroless deposition, or via chemical etching of metal foil. The wire 12 can be made of platinum, gold, iridium, tantalum, palladium, rhodium, rhenium or alloy thereof, where said wire 12 is preferentially encapsulated in a bioinert polymer layer 13, such as a polyfluorocarbon, specifically the fluoropolymer FEP, where such polymer layer 13 is about 20–500 $\mu$m thick, preferably about 20–30 $\mu$m, where the cross-sectional area of said wire 12 is about 0.0005–0.1 mm$^2$ preferably about 0.01 mm$^2$. Said coil has an outer diameter of about 15–30 mm and an inner diameter of about 10–20 mm, preferably an outer diameter of about 20 mm and an inner diameter of about 15 mm. Such coil design has the advantage of having a thin profile, being flexible to better conform to the skull radius and occupying a minimum footprint between the skull and overlying skin. A key inventive feature of said coil 4 is that it is located away from interfering metal materials, especially magnetic materials, thereby improving the inductive power coupling efficiency across the skin surface between the internal and external coils.

Alternately, any conductor material encased in a biocompatible material or enclosed in a biocompatible container may be used to fabricate said coil.

FIG. 1 also illustrates some "identification markers" 5, preferentially dots, squares, bars or similar symbols, located with the inside perimeter of the coil 4, which markers 5 can be used to post operatively identify the serial number, model number and/or date of the implanted part 1, such identification being useful for future reference where such datum is not readily available using other means. Said marker can be fabricated from a biocompatible metal such as platinum, gold or titanium encased, or not, in a carrier material, and identified, in vivo, using medical imaging, for example, X-rays or a CT scan. Any marker designs can be used, at any locale attached to, or near, the implanted part of the invention for post implant identification, such designs being within the scope and spirit of the invention. Since the resolution of X-rays scans is about 0.3 mm, it is also possible to simply use letters, numbers or such similar symbols for the serial number, model number or date for implant identification.

The microphone 9 is preferably a small commercially available microphone, where said microphone 9 is hermetically encapsulated in a biomaterial (such as titanium) casing 14, with a thin diaphragm 15 covering one end of said casing 14 where acoustic input is preferred. However, any hermetically sealed microphone could be adapted for said application.

The microphone casing 14 and electrode array 10 are connected to the housing sections 2 and 3 via junction 16 where cables 7 and 8 merge. Cables 7 and 8 (hereinafter referred to as connections 7 and 8) are each contain a plurality of biocompatible wires, preferably made of lithographically formed electro deposited platinum, where said wires are encapsulated in an inert polymer layer, such as the fluorocarbon FEP, where such polymer layer 17 is about 20–200 $\mu$m thick, preferably about 25–50 $\mu$m, where the cross-sectional area of each of said wire is about 0.0005–0.5 mm$^2$ preferably about 0.01– 0.05 mm$^2$. For surgical convenience, said connections 7 and 8 are folded longitudinally (ie. pleated) to create 2–8 layers so as to minimize the cable width. Also, said connections 7 and 8 are preferably "corrugated" 17 over all or part of said connections so as to enable the connections 7 and 8 to expand with minimum stress during surgical handling, skull growth and any movement of the implanted components post surgery. Such corrugations 17, which are simply formed by first heating, then cooling, the polymer film in a corrugating jig, must be sufficient to allow for at least about 20–40 mm of expansion in each of the connections 7 and 8 to allow for normal skull growth from infant to adult. A review of other configurations that allow for subcutaneous stretching of wires due to growth is described in, for example, "Evaluation of Expandable Leadwires for Pediatric Cochlear Implants", by Shi-ang Xu, et. al., Amer. J. Otology, vol. 14, No. 2, March 1993.

Figure 2:
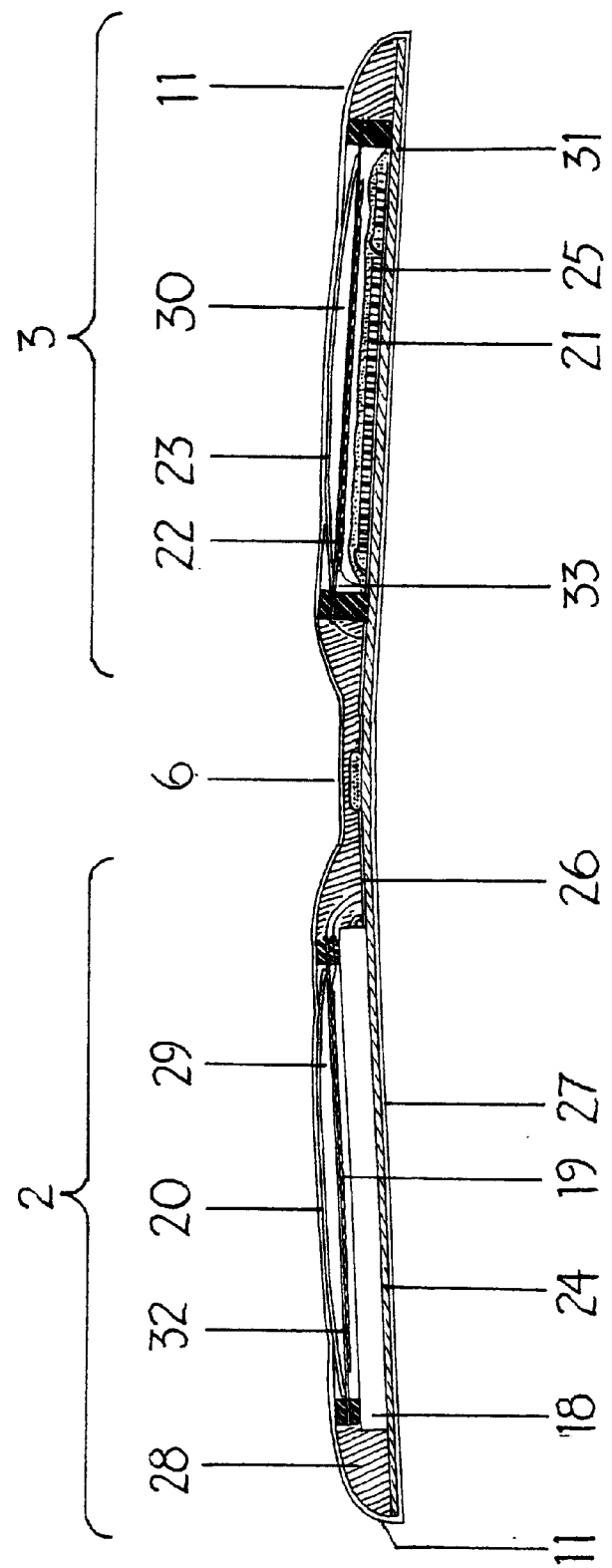
FIG. 2 illustrates a cross-sectional view of the two housing sections, including the key components therein, and the connecting bridge between said sections.

FIG. 2 illustrates a cross-sectional view of the housing sections 2 and 3, and bridge section 6, showing the internal components thereof, namely, the battery 18, piezoceramic 19 (and snap dome 20) for the panic "off/on" switch, and the electronics 21 (for example an ASIC chip), the piezoceramic 22 (and snap dome 23) for the volume control. The location of said components within the housing sections 2 and 3 is for illustration purposes only. It will be appreciated that other relative locations of the components within the housing are possible.

Said housing sections 2 and 3 are both preferably substantially circular, both sections being thin and having a relatively rounded profile at the edges 11. The sections are joined by a pliable (or bendable) bridge 6.

The internal components within each housing section 2 and 3 are mounted on ceramic substrates 24 and 25, where such substrates are each approximately 50–500 $\mu$m thick, preferably about 250 $\mu$m, and where said substrates 24 and 25 contain a plurality of electrically insulated electrical lead-throughs. The underside of said ceramic substrates 24 and 25 are laminated to the polymer film 26 containing platinum wires. The underside of said film 26 is then laminated to a gold foil substrate 27, said gold foil 27 being approximately 25 $\mu$m to 250 $\mu$m thick, preferably about 50–75 $\mu$m thick, said foil 27 also forming the key support structure for the pliable bridge x.

Since said internal components are not all biocompatible, it is essential to hermetically encapsulate the internal components (mounted on the ceramic substrates 24 and 25) from ingress of body fluids and or leakage of component material into the body tissues, which can be partially accomplished using a medical grade epoxy. Said medical grade epoxy (or any biocompatible polymer) 28 is used to coat and encapsulate the internal components, but not the outside edges of the ceramic substrates 24 and 25, and excepting the gold (or platinum) foil over the snap domes 20 and 23, and excepting for the alternate embodiment, the surface of the PVDF piezo films. Of course, air or gas pockets 29 and 30 are required for operation of the snap domes 20 and 23. Additionally, air or gas pockets 29 and 30 are required for operation of the piezoceramics 19 and 22, where air or gas in all said pockets are slightly compressed during the action of the snap domes 20 and 23, and piezoceramics 19 and 22. Said epoxy 28 and 31 also provides a smooth shape to the external surface of housing sections 2 and 3. Alternately, any encapsulant material can be used as a substrate material to provide shape to the overall housing. The epoxy surfaces 28 and 31 are then covered, in one or more steps, with a layer of gold, preferably using well established vacuum deposition techniques, or alternatively, using electroless deposition, to create a thin layer of gold, about 0.01 $\mu$m to 10 $\mu$m thick, preferably about 0.1–1.0 $\mu$m thick. Said thin gold layer is subsequently thickened to about 10 $\mu$m to 500 $\mu$m, preferably about 25 $\mu$m to 75 $\mu$m, using established electro gold plating technology. Said gold layers are designed to bond directly to the outside edge of the ceramic substrates 24 and 25, thus creating a sealed, hermetic covering over the components mounted onto each of the ceramic substrates 24 and 25. Alternately, epoxy surfaces 28 and 31 are first covered, in one or more steps, with palladium using an electroless deposition process, and, in a further embodiment, thickened with gold. Other alternate embodiments include coating the outer gold layers with titanium (or platinum), and/or with medical grade silicone.

The gold or platinum (or, in the case of an all titanium or titanium/ceramic enclosure, titanium) foil over the snap domes 20 and 23 is pliable and thus beneficial for the manual operation, through the skin surface, of the underlying piezoceramics 19 and 22, so as to engage the panic "off/on" and volume "up" and volume "down" controls.

For the preferred embodiment, snap domes 20 and 23 are used for optimizing the operation of the piezoceramic actuators 19 and 22, where said actuators are each preferably mounted to a flexible support disc, 32 and 33. For a given pressure, said piezoceramic actuators 19 and 22 generate a much larger voltage spike when the snap domes 20 and 23 suddenly "snap" at a predetermined force when pushed, such action causing the piezoceramic material to very slightly bend (or flex) in a short time period thereby creating a substantially repeatable defined strong voltage pulse, said pulse being sufficient for activating the electronics. Also, the snap domes provide a convenient tactile feedback to the implantee indicating that the switch has been activated. Said snap domes are available from, for example, from Snaptron Inc., Loveland, Colo.

FIG. 2 also illustrates the implanted rechargeable battery 18 housed within housing section 2. Alternately, a capacitor can be used as a short term rechargeable power storage device. Said battery 18 can be conveniently recharged, transcutaneously, from time to time, using an external device 51 (see FIG. 9) to inductively couple power to the internal coil 4, such power transfer able to charge the internal battery 18 using appropriate electronics.

The technology for implanting long-lasting secondary (ie. rechargeable) batteries, especially lithium type cells, in the human body is not well established. The key criteria are: (a) safety, (b) longevity and (c) charge capacity. Published studies have reviewed these issues (see for example, "Preliminary Evaluation of Rechargeable Lithium-ion Cells for an Implantable Battery Pack", by G. K. MacLean, et. al., J. of Power Sources 56 (1995) 69–74). The use of a primary cell is not practical for cochlear prostheses, since the power consumption is too high, being much higher than, for example, pacemakers. Although a number of rechargeable lithium type batteries are commercially available, they are generally not considered safe for implantation. The use of other battery chemistries, such as nickel metal hydride, is possible for implantation, albeit for only limited periods of time due to the limited number of charge/discharge cycles possible before said battery can no longer be effectively recharged. The preferred embodiment of the present invention uses a lithium chemistry battery developed by John Bates, et. al. of Oak Ridge National Labs, described in "Thin Film Rechargeable Lithium Batteries for Implantable Devices", ASAIO Journal, vol. 43, no. 5, 1997. Such a battery has high charge density, is substantially rechargeable over tens of thousands of cycles, and uses a solid state electrolyte, namely, lithium phosphorous oxynitride. Although such a battery meets the key criteria for a safe, long lasting rechargeable implantable battery, no data are as yet available with respect to long term implant usage.

With respect to the electronics, the preferred embodiment is an ultra low power analog circuit design, the basic theory of which is described in a Ph. D. Thesis by Walter Germanovix, October, 1998, Imperial College of Science, Technology and Medicine, University of London, U.K., to process the speech signals from the microphone to electric current signals to be sent to the electrode array 10. An alternate embodiment uses a more conventional DSP design in a relatively compact package, although such a design requires more power and space to operate than the analog design.

The electronics for the battery charger circuit and other controls use established technology.

Figure 3:
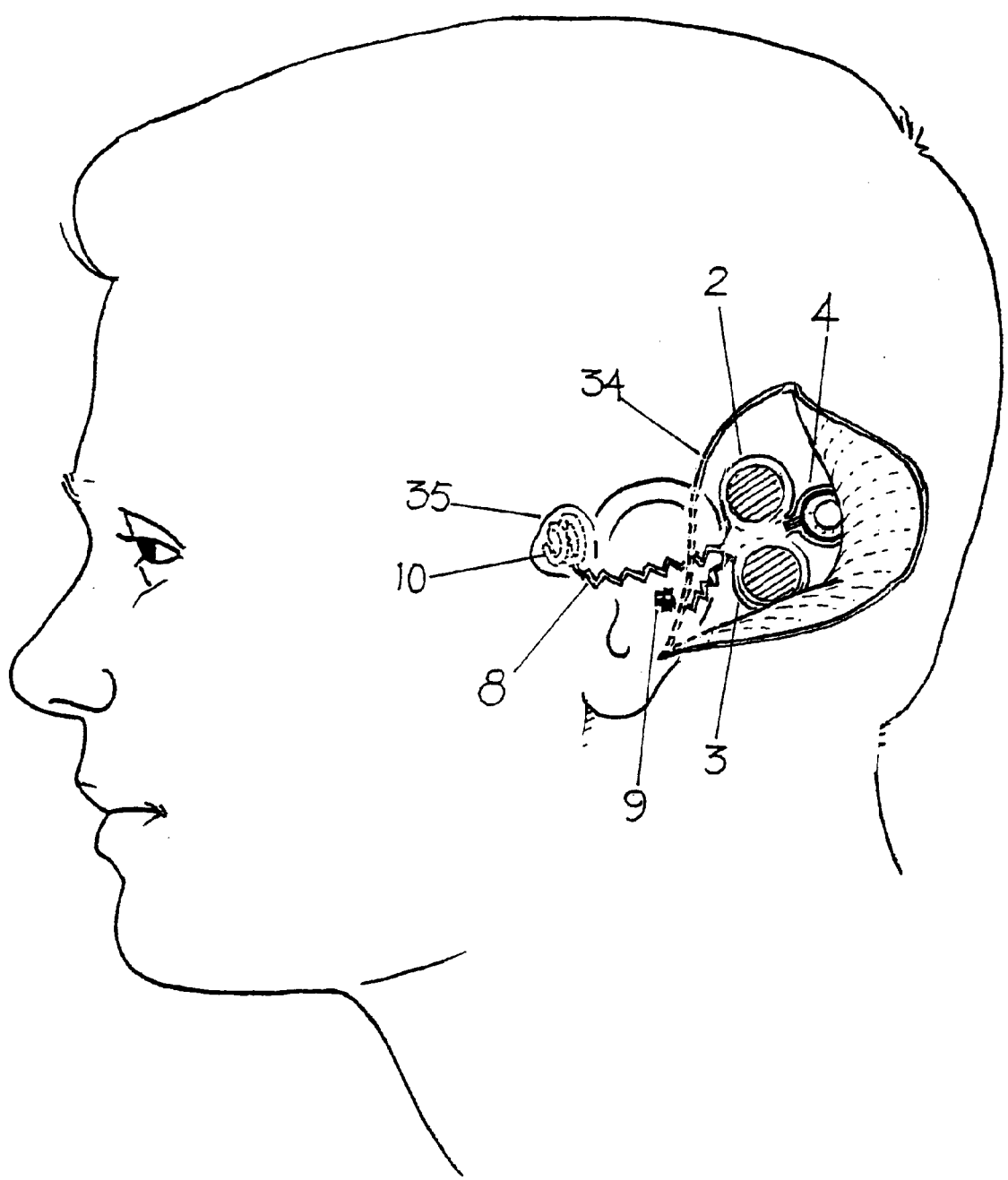
FIG. 3 is a lateral view of the left side of the head showing the implanted parts of the invention in place, said view also illustrating one embodiment of an incision on the head to gain access for implantation.

FIG. 3 is a lateral view of the left side of the head illustrating the preferred location of the implanted part 1, showing housing sections 2 and 3, bridge 6, coil 4, corrugated connections 7 and 8, microphone 9 and electrode array 10. Surgical implantation of said invention can be accomplished during a local or total anaesthetic. Line 34 illustrates one incision whereby the surgeon raises a postauricular flap to implant the various parts of the invention. The thin housing sections 2 and 3 can be placed against the skull, or even adjacent the dura in infants, without excavating skull bone to recess such housing sections. The microphone 9 is positioned behind the skin in the posterior wall of the external auditory canal, whereas the electrode array 10 can be inserted by any approach which gives access to the round window or basal turn of the cochlea 35. However, the preferred surgical procedure is preferably carried out by either a mastoidectomy and facial recess approach, or by a transcanal approach or by a combination thereof at the surgeon's discretion.

An alternate embodiment involves having the surgeon recess one or both housing sections 2 and 3 in a small excavation of the outer plate of the skull, or against the dura in an infant, or even between the dura and the skull in a small infant. As the invention has no external behind-the-ear speech processor (as in some of the current commercial devices) the housing sections 2 and 3 do not have to be placed more than about 4.5 cm behind the postauricular skin crease to avoid conflict with a behind-the-ear mounted device. In fact, the housing sections 2 and 3 can be placed as close to the skin crease as the surgeon wishes. These factors offer a significant reduction in the surgical time compared to that now required for implanting conventional cochlear devices. There is also less anesthetic time needed, and in view of the lesser dissection, a quicker healing process from the surgical intervention is expected. Such modified surgical procedure also allows for implantation using only local anesthesia, and would be especially suitable for young infants, or the elderly, or those with other disabilities who cannot tolerate extensive surgery or general anesthesia, thus extending the range of persons that can be implanted using the invention, and reducing surgical cost and risk.

Figure 4:
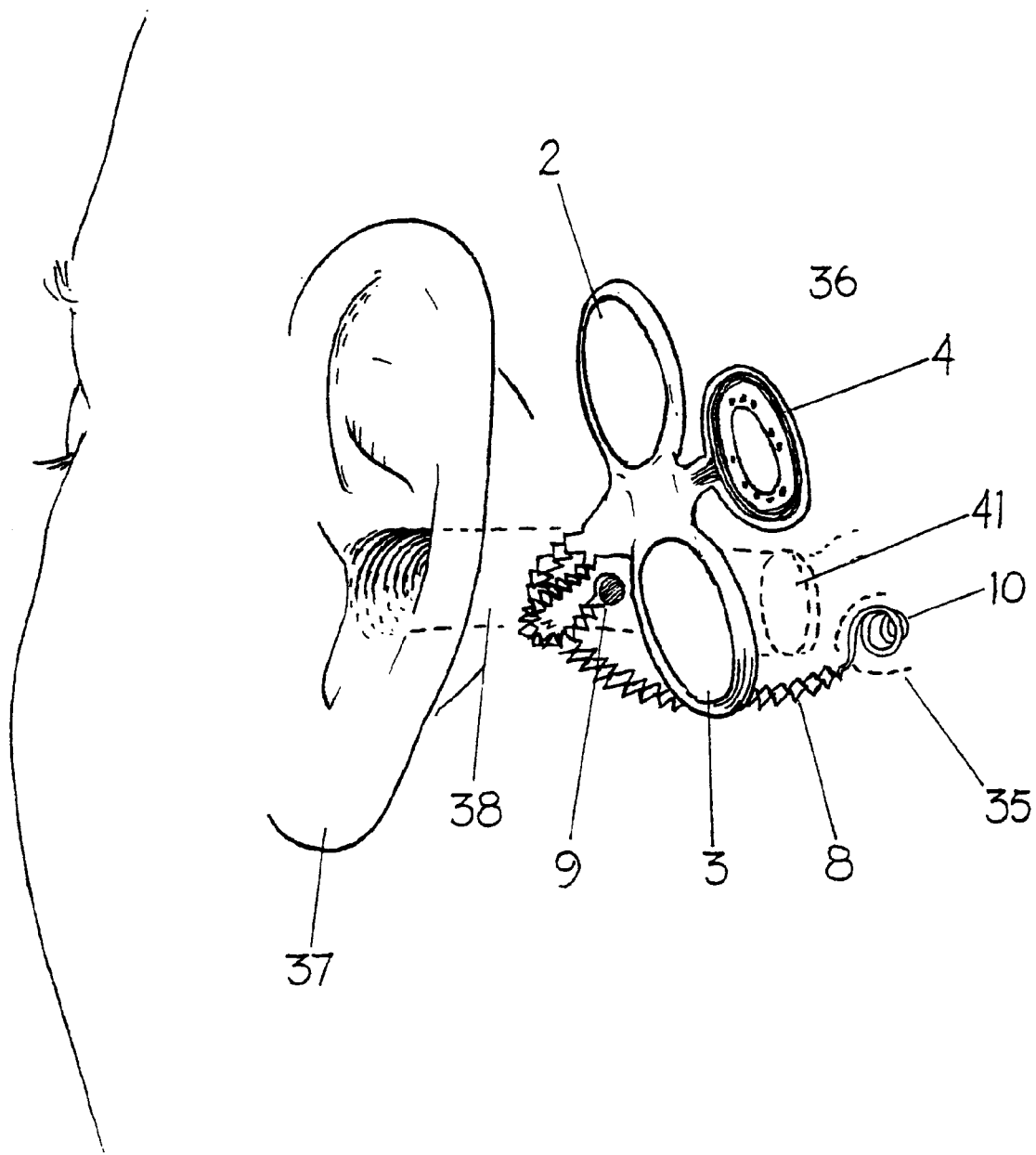
FIG. 4 illustrates an posterio-lateral view of the implanted part of the invention in place, said view also showing the coil, the two housing sections (placed against the skull, posterior of the pinna), the microphone (anchored within the auditory canal) and the electrode array (positioned within the cochlea).

FIG. 4 illustrates a posterior-lateral view of the surgical area showing the implanted part of the invention with the coil 4 and housing sections 2 and 3 placed against the skull 36 posterior to the pinna 37, the microphone 9 (the housing of which is shown positioned posteriorly, as two circles with dashed lines) anchored within the auditory canal 38 and the electrode array 10 positioned within the cochlea 35. A key feature of said implanted part 1 is that the housing sections 2 and 3, and coil 4 are sufficiently thin, preferably less than about 2.0–2.5 mm in thickness, to allow these devices to be placed directly against the skull surface 36, or between the skin layer covering the skull, without the need to surgically excavate skull bone, where said housing sections 2 and 3 can be sutured to the overlaying skin, or anchored to the underlying skull 36 with suture lines or screws, so as to minimize movement of said housing sections post operation.

Figure 5:
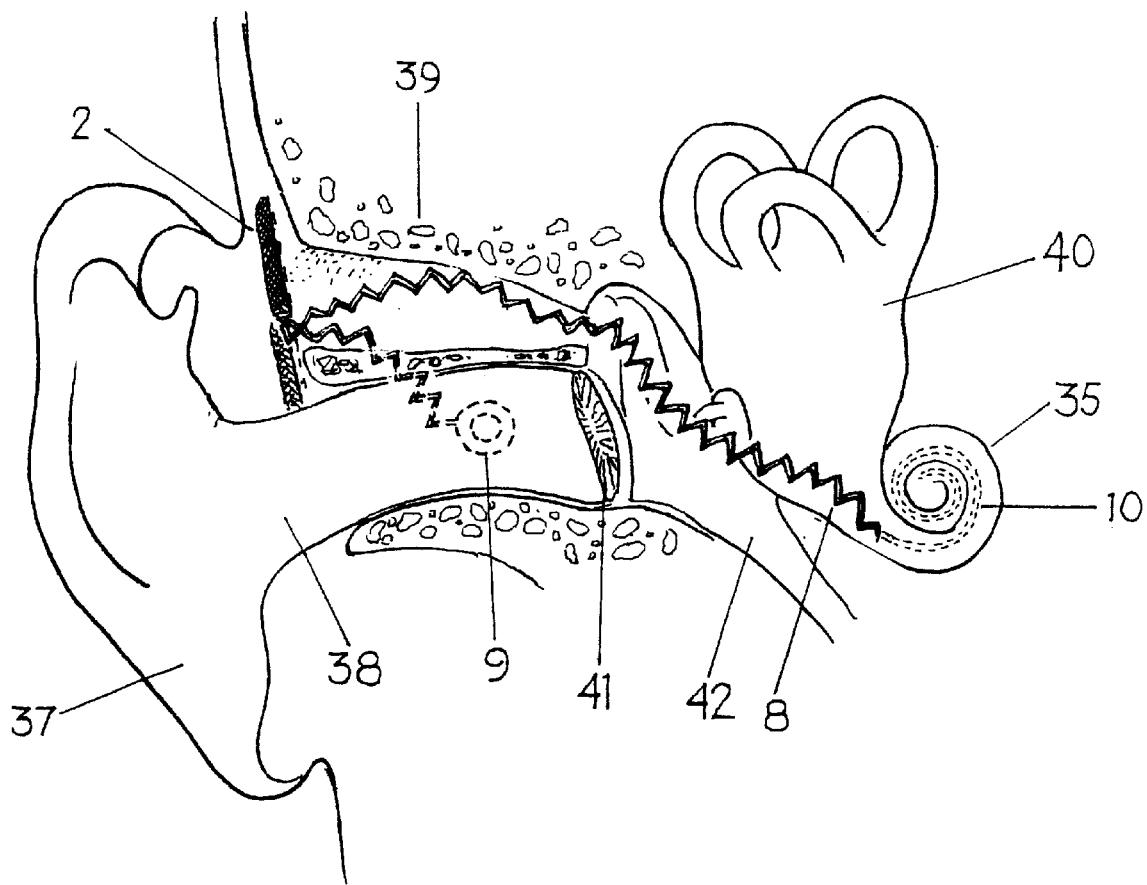
FIG. 5 shows a coronal diagrammatic view of the pinna, auditory canal, mastoid cavity, tympanic membrane, semicircular canals, and cochlea, with the implanted parts of the invention in place.

FIG. 5 shows a coronal section of the pinna 37, auditory canal 38, mastoid 39, semicircular canals 40, tympanic membrane (or eardrum) 41 and cochlea 35, with the implanted part of the invention in place. The surgeon can enter the middle ear 42 via the mastoid cavity 39 preferably using a local anaesthetic.

Figure 6:
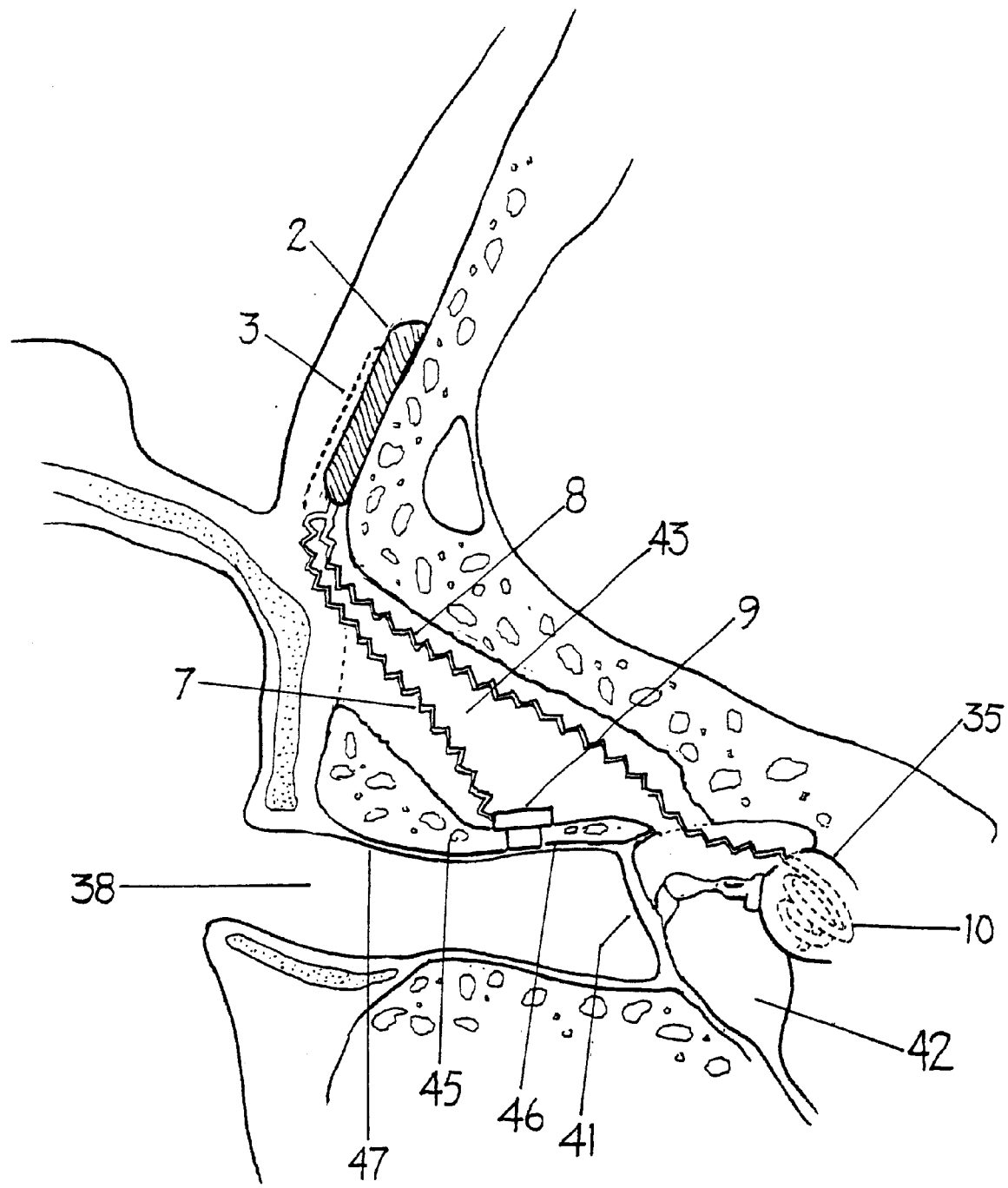
FIG. 6 depicts a horizontal cross-sectional view of ear canal, mastoid, middle ear and cochlea, illustrating an inventive surgical approach requiring only one cavity excavation to gain entry for both the electrode array and microphone.

FIG. 6 depicts a cross-sectional horizontal view of the ear canal 38, middle ear 42 and cochlea 35 illustrating a surgical approach having only one cavity excavation 43 to gain entry for both the electrode array 10 and microphone 9. An introducer, which is thin enough to pass through the retrofacial triangle can be used for inserting the electrode array 10 into the cochlea 35 through a smaller bony dissection than is now possible using conventional techniques. Microphone 9 is implanted substantially in the locale of the posterior wall 45 of the external auditory canal 38, such location taking advantage of the natural resonance of said auditory canal 38. Sound pressure in the auditory canal 38 near the location of the microphone 9 is advantageously enhanced, especially for some key voicing frequencies (see for example, A. E. Deddens, et. al., Am. J. Otolaryngol, 11:1–4, 1990; and J. A. Feigin, et. al., Ear and Hearing, Vol. 11, No. 5, 1990). To position the microphone 9, the surgeon first creates a small mastoidectomy cavity and elevates the skin of the posterior wall 47 of the external auditory canal 38. The bony wall 46 between the mastoid cavity 43 and the external auditory canal 38 is thinned. A hole is created in the posterior wall 47 of the external auditory canal 38 about half way between the tympanic ring and the meatus of the external canal 38. This hole is made substantially to the dimensions of the microphone housing 9, using an appropriately sized drill bit and a custom designed hand tool. Facia is packed around the microphone housing 9 to secure it in position.

Figure 7:
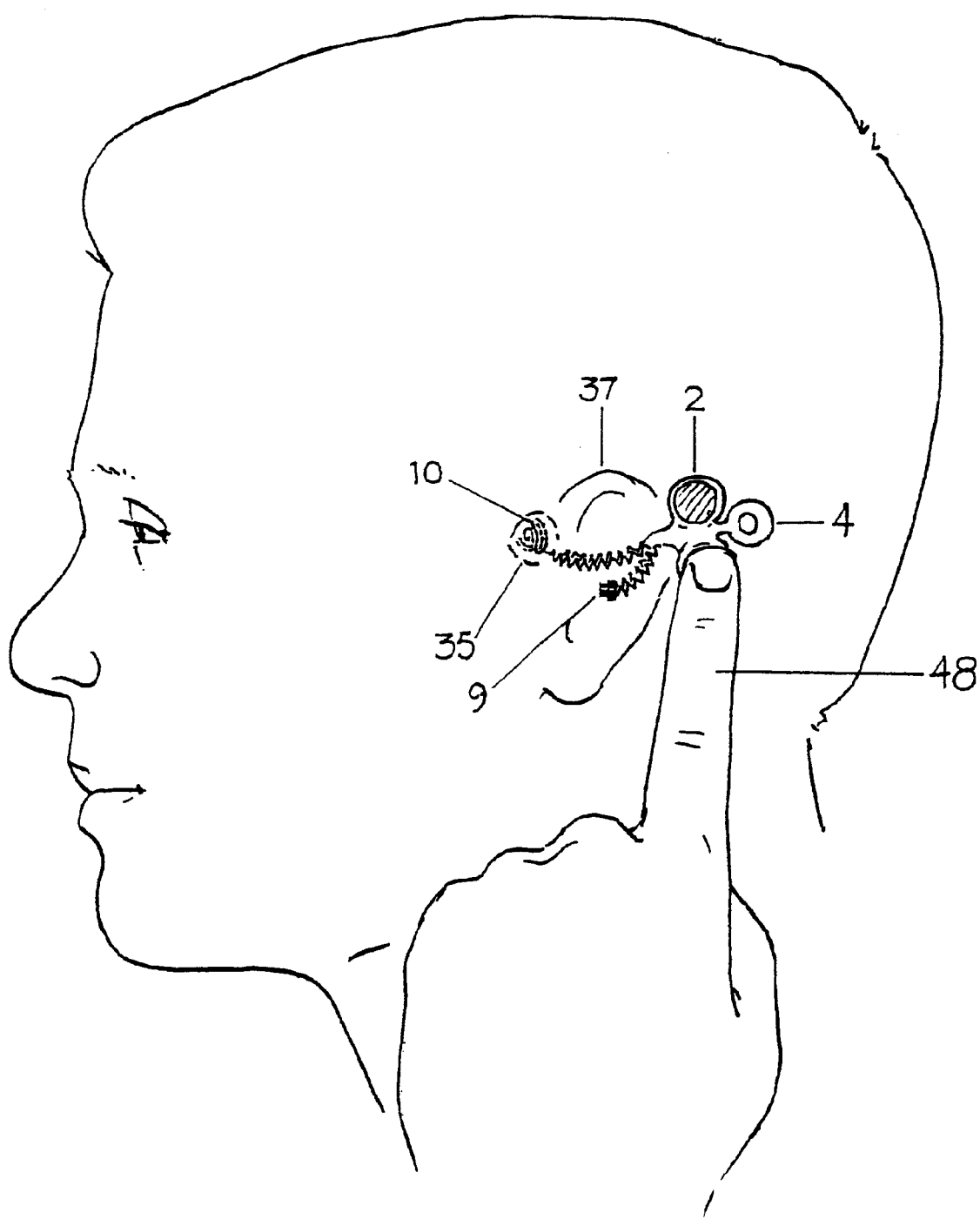
FIG. 7 depicts a lateral view of the left side of the head illustrating a convenient method for activating the volume control switch by pressing, with a finger, against the surface of a housing section. (The skin covering said housing section is not shown).
Figure 8A:
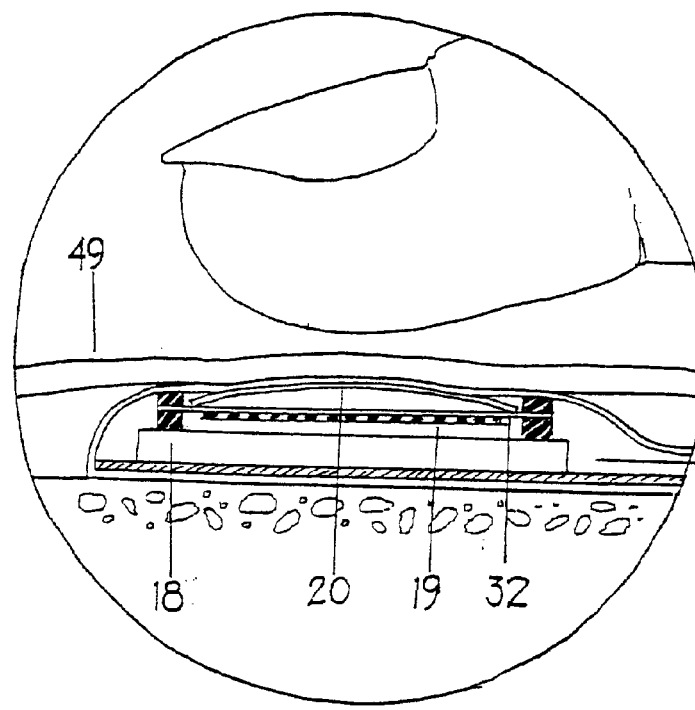
FIG. 8a depicts a cross sectional view of a housing section, positioned subcutaneously against the skull, showing a finger located just above the skin overlaying the snap dome contained within said housing section.
Figure 8B:
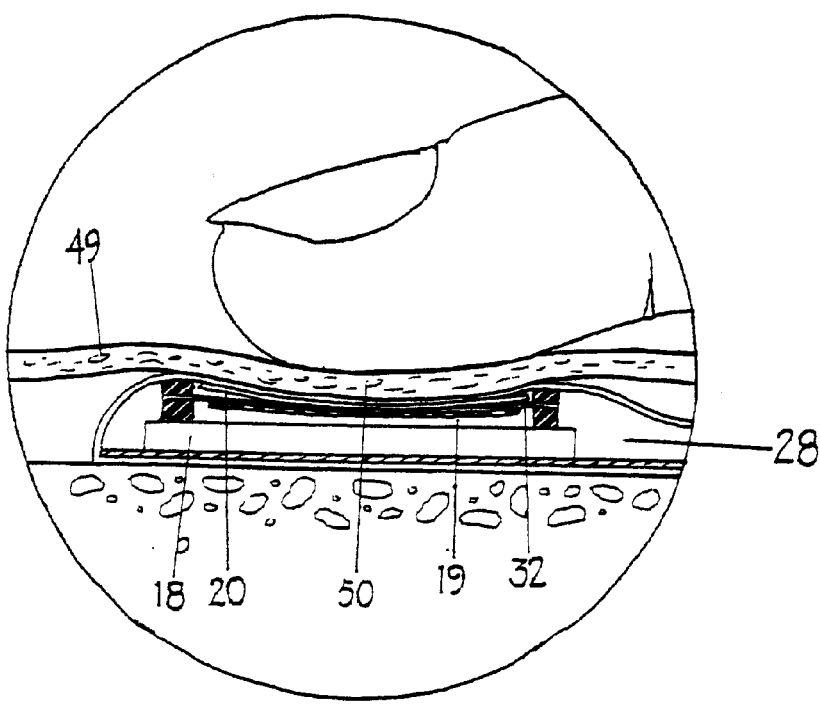
FIG. 8b depicts a cross sectional view of a housing section, positioned subcutaneously against the skull, showing a finger compressing the skin and the underlying snap dome, causing the snap dome to "snap" and the piezoceramic disc underlying the snap dome to slightly bend.

FIG. 7 illustrates a lateral view of the left side of the head showing a convenient method for activating the volume (or panic "off/on") switches by using a finger 48 to push against the skin covering housing sections 2 or 3. (Note that the skin covering said housing sections 2 and 3 is not shown for clarity of illustration). FIGS. 8a and 8b illustrate the details of the activation method shown in FIG. 7. FIG. 8a shows finger 48 against skin 49 overlaying housing section 2. FIG. 8b shows finger 48 pushed against skin 49 said skin 49 being compressed 50, thereby causing snap dome 20 to suddenly "snap" and impact against support disc 32, said impact causing piezoceramic element 19 to slightly flex creating a voltage. Said voltage is sensed by the electronics in housing 3 to control volume (or panic "off/on"). A similar snap dome activation switch is incorporated into housing section 3. The choice of which housing section in which to locate the electronics and battery is not critical, nor is the choice as to which housing section contains the volume or panic "off/on" switch.

Figure 9:
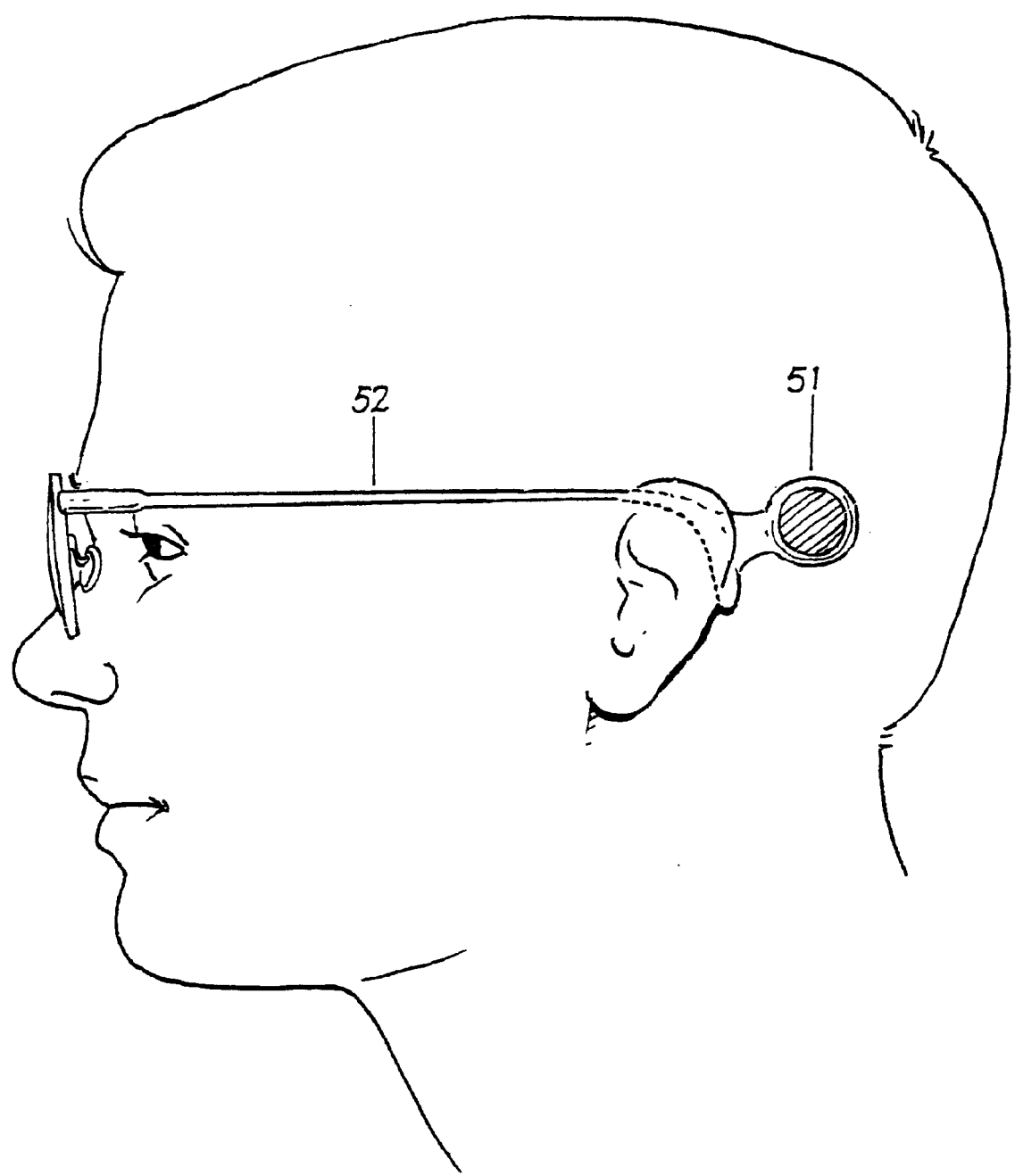
FIG. 9 is a lateral view of the left side of the head showing a stand-alone charging device, containing a coil, battery and electronics, said device mounted onto a standard eyeglass frame, such that said coil is positioned substantially over the internal coil.

FIG. 9 is a lateral view of the left side of the head showing the preferred embodiment, with an external part 51, containing a coil, battery and electronics, mounted onto a standard eyeglass frame 52, said external part 51 positioned substantially over the internal coil 4 (shown in FIG. 3). Such external part 51 can be conveniently held to the head by the user from time to time to recharge the implanted battery, or in an alternate embodiment, to recharge any electrical storage device contained within the implanted part. The use of a standard eyeglass frame allows a convenient and aesthetically acceptable method to accurately and repeatably position the coil in said external part 51 substantially over the internal coil 4 (shown in FIG. 3), so as to inductively couple power and data between the external and internal coils.

Figure 10:
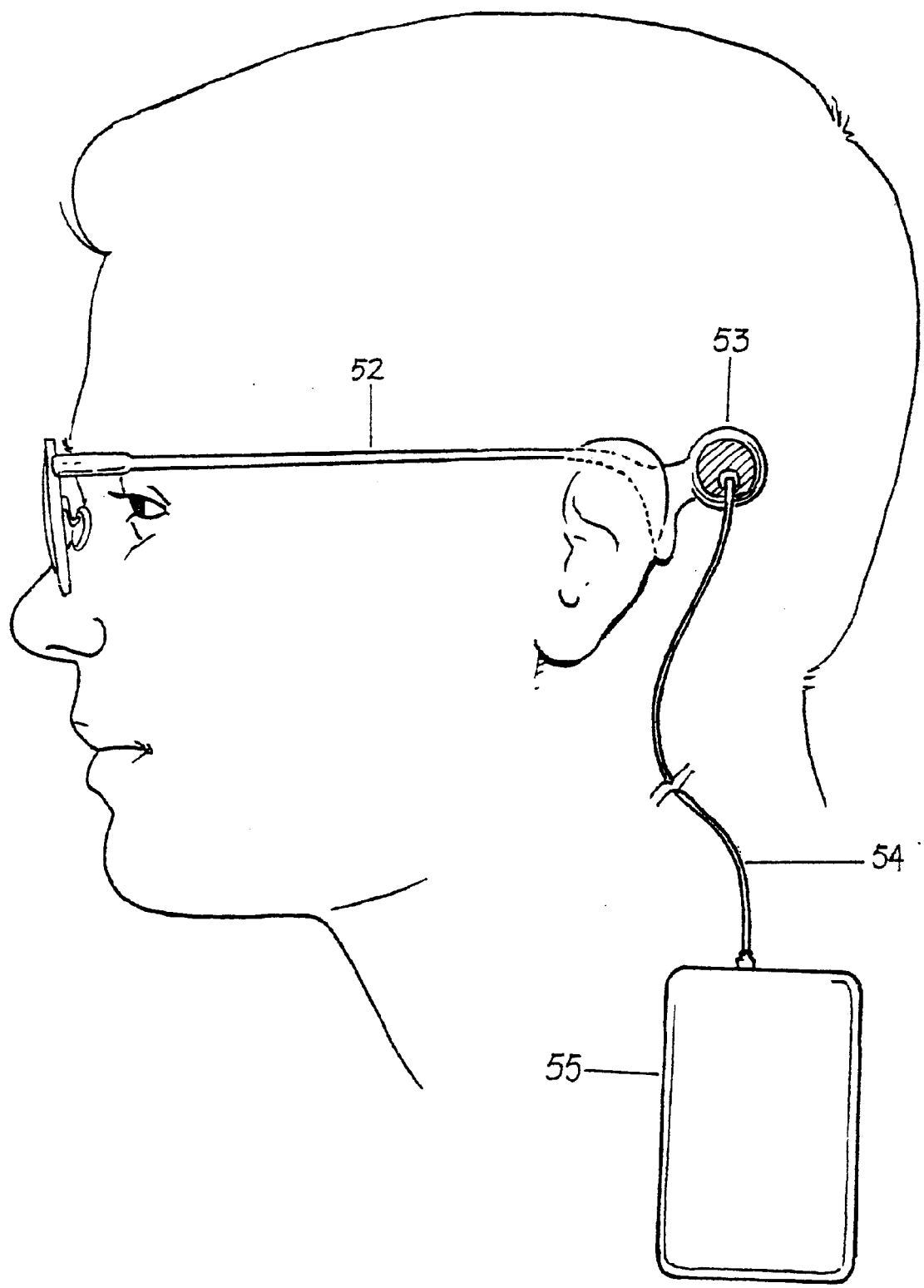
FIG. 10 is a lateral view of the left side of the head showing a remotely powered coil, said coil mounted onto a standard eyeglass frame and attached via wires to a body-worn device, said device containing battery and electronics.

FIG. 10 is a lateral view of the left side of the head showing an alternate embodiment, with a coil 53 attached to eye glass frame 52, with said coil 53 positioned substantially over the internal coil 4 (shown in FIG. 3). Power to coil 53 is supplied by wires 54 attached to a remotely located energy source 55 said source powered by a body-worn primary or secondary battery, or, alternately, by AC wall plug power.

Figure 11:
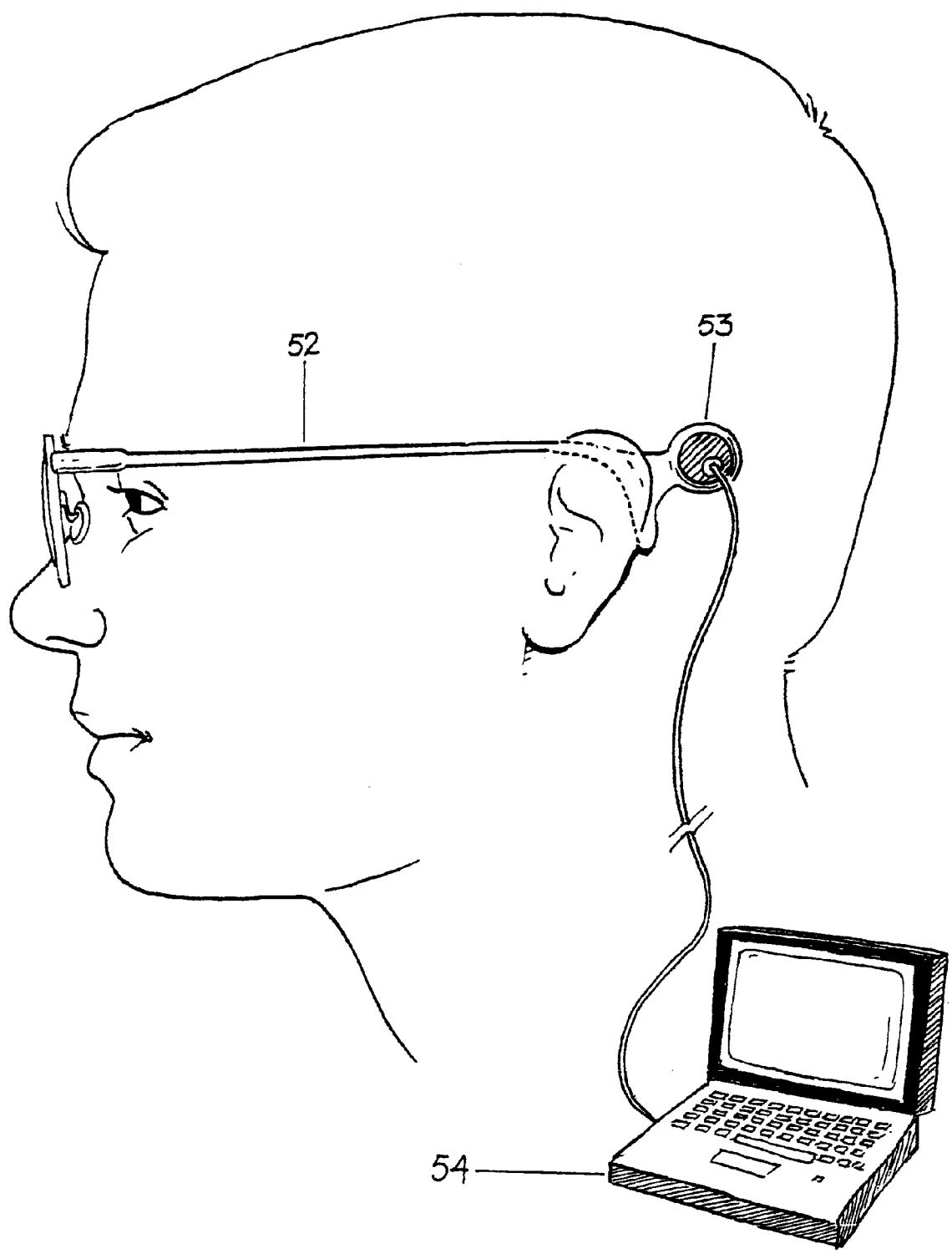
FIG. 11 is a lateral view of the left side of the head showing a remotely powered coil, said coil mounted onto a standard eyeglass frame and attached via wires to a device, such as a computer, for programming and or modifying, via an inductive link, the parameters within the implanted electronics.

FIG. 11 is a lateral view of the left side of the head showing one method for programming and or modifying the parameters within the implanted electronics. Such programming can be conveniently accomplished post-operatively, from time to time, by inductively coupling data between the internal 4 and external 53 coils using a computer 54, or similar control device, attached to the external coil 53.

Figure 12:
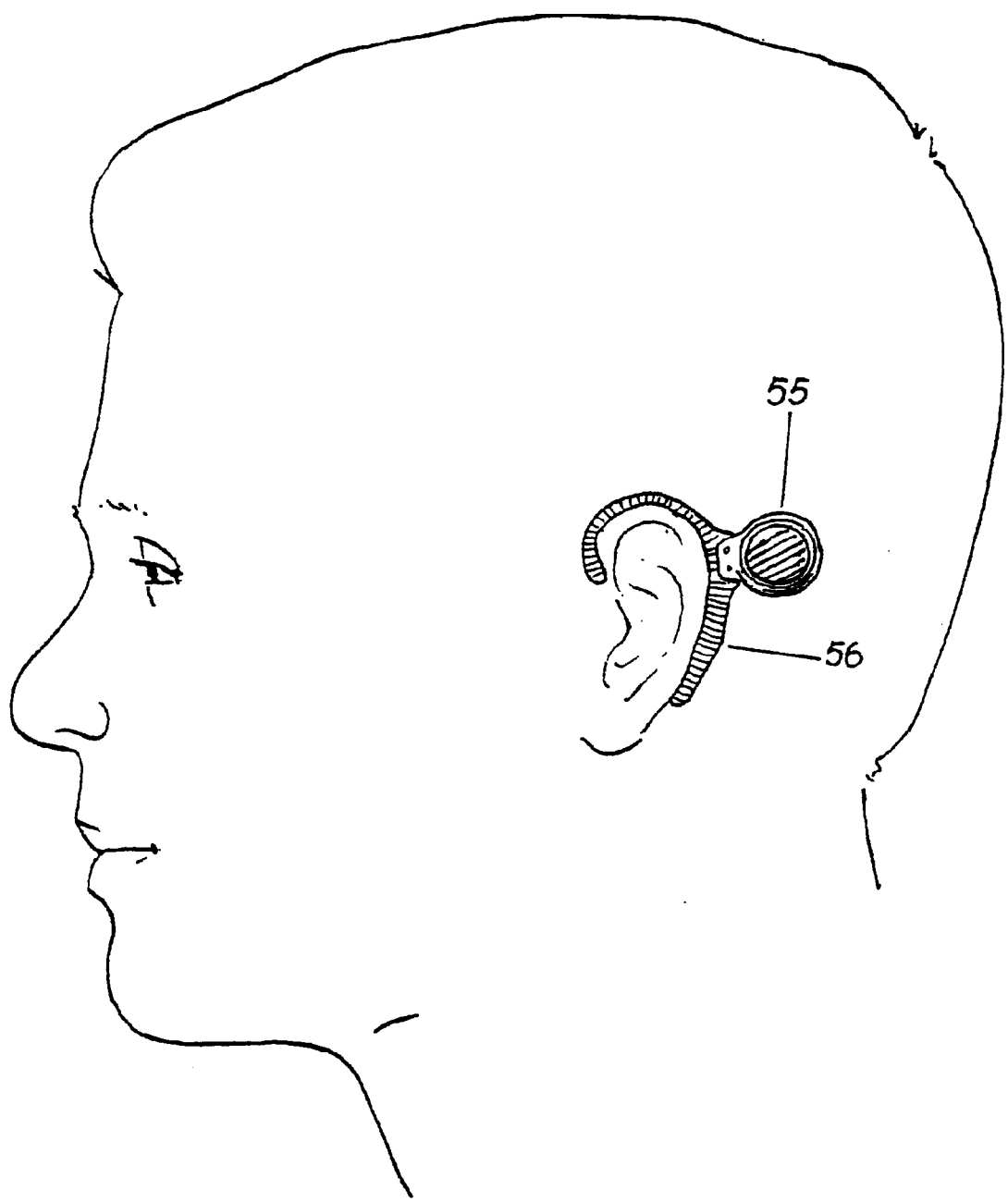
FIG. 12 is a lateral view of the left side of the head showing an alternate method, similar to that shown in FIG. 9, for positioning the external coil substantially over the internal coil so as to charge the internal battery.

FIG. 12 is a lateral view of the left side of the head showing an alternate method, similar to that shown in FIG. 9, for positioning an external device 55 (containing a coil, electronics and a battery) substantially over the internal coil 4 so as to charge the internal battery 18. Such alternate method uses a modification of a conventional BTE (behind-the-ear) hearing device as the mechanical support structure 56 onto which said external device 55 is mounted. A further embodiment is to mount only the coil on the BTE frame 56, and supplying power and/or data to said coil using an external power and/or computer similar to that shown in FIGS. 10 and/or 11.

Figure 13:
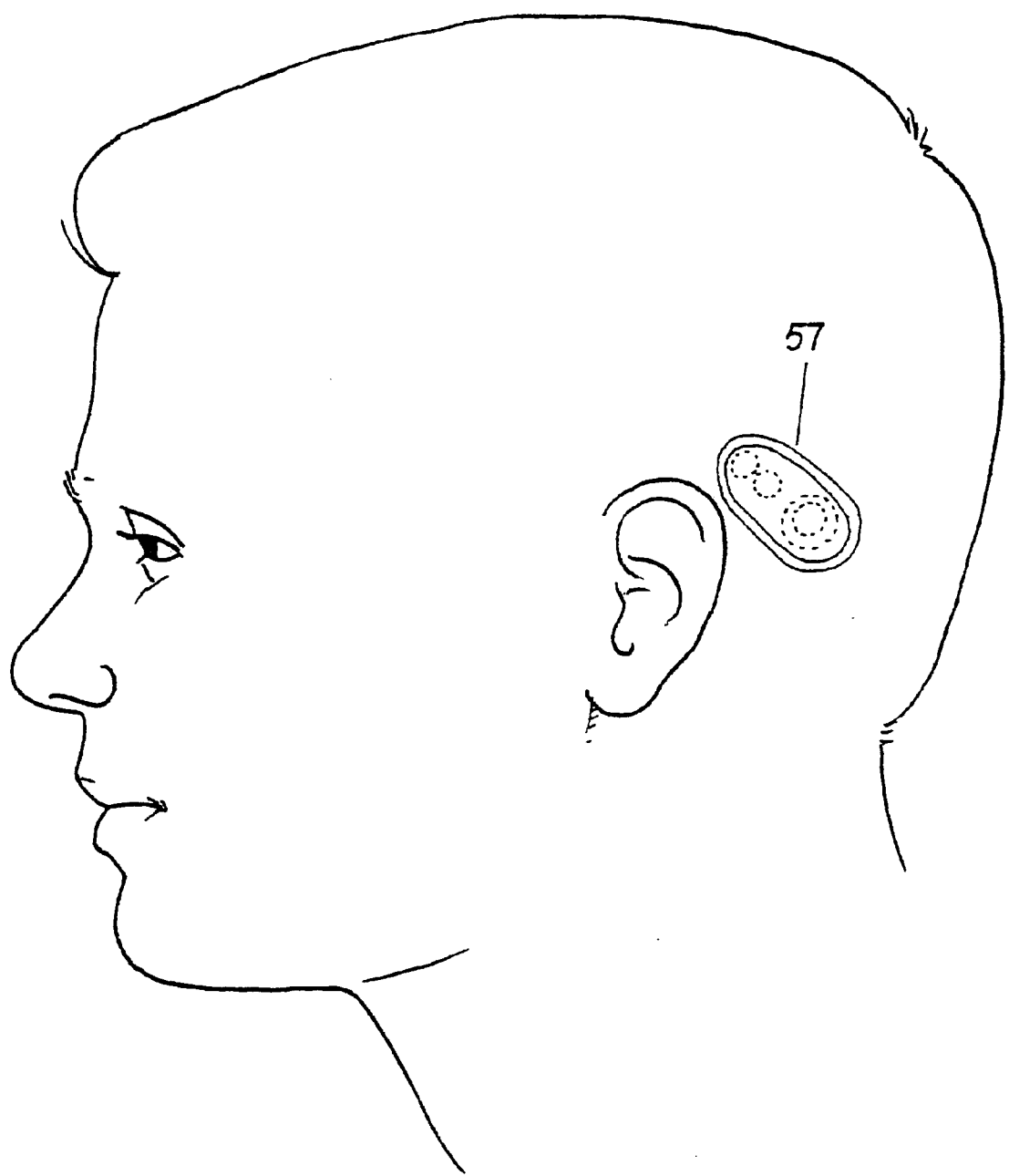
FIG. 13 is a lateral view of the left side of the head showing a stand-alone charging device, containing a coil, two magnets, battery and electronics, said device both magnetically attached to the head, and also configured such that said two magnets rotationally align with two opposing internal magnets, such rotational alignment of said charging device ensuring that said coil is positioned substantially over the internal coil.

FIG. 13 shows a lateral view of the left side of the head with the external part 57 (containing a coil, battery and electronics) magnetically attached to the head using opposing magnets, with at least two internal magnets and at least two magnets outside the head. Most conventional cochlear prostheses use such opposing magnets (one internal and one external) to hold an external device to the head. The magnets in such conventional devices are generally contained within the perimeter of the coil to align the external and internal coils, such arrangement acting to reduce the inductive power coupling due to presence of a conductive material within the RF inductive field. An inventive feature of the device is shown in FIG. 13, where the magnets and coil are not coaxial.

Figure 14:
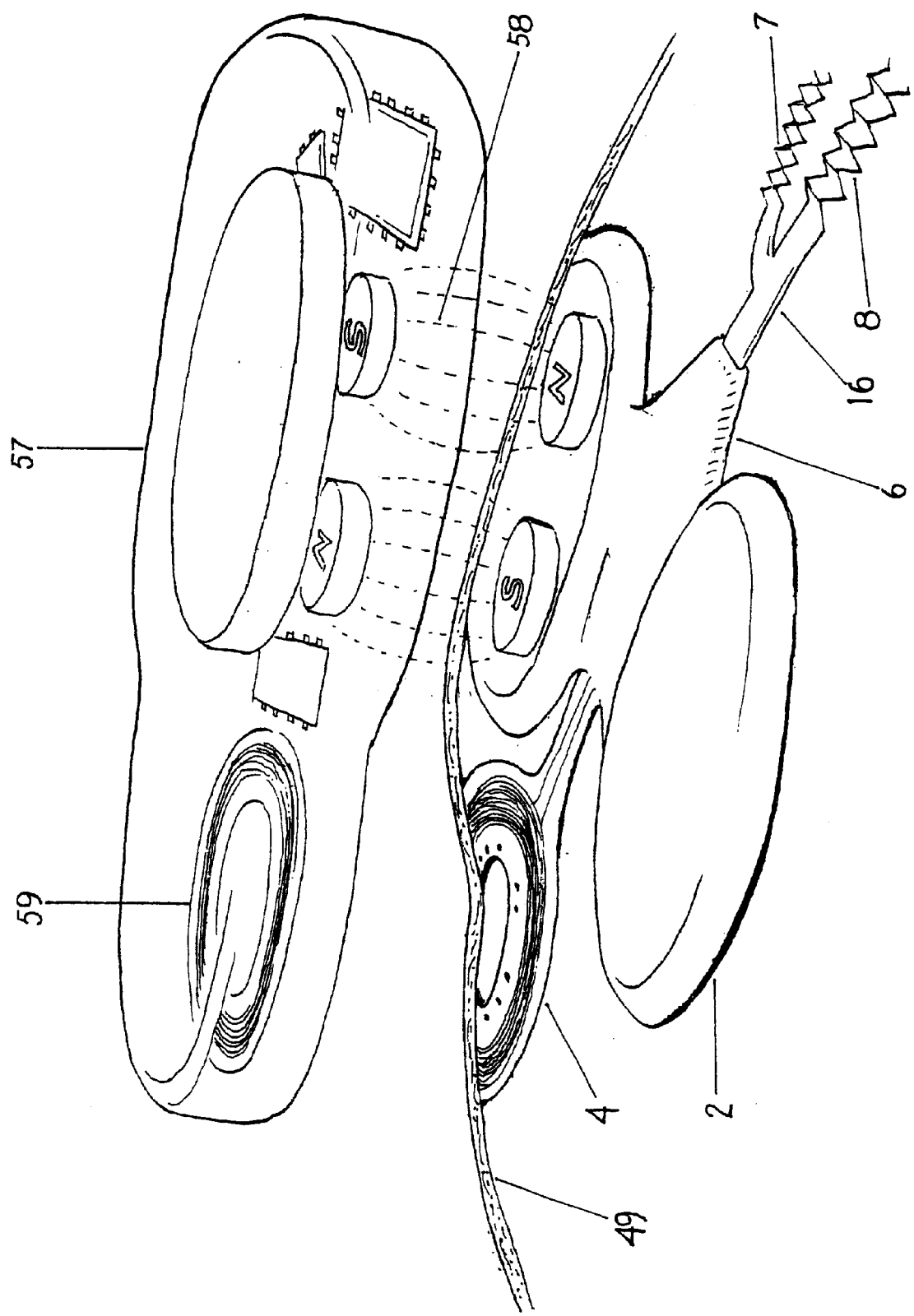
FIG. 14 illustrates one embodiment to achieve rotational alignment of opposing magnets contained within the stand-alone charging device shown in FIG. 13, and opposing magnets contained within one housing section of the implanted part, so as to substantially align the external coil and implanted coil, one over the other.
Figure 15:
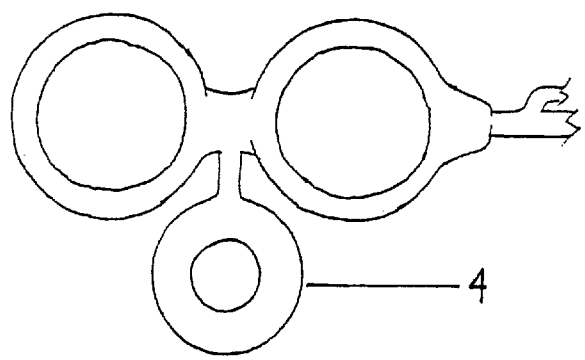
FIG. 15 illustrates an alternate embodiment for the configurations of the coil and two housing sections, where the coil is inferior.
Figure 16:
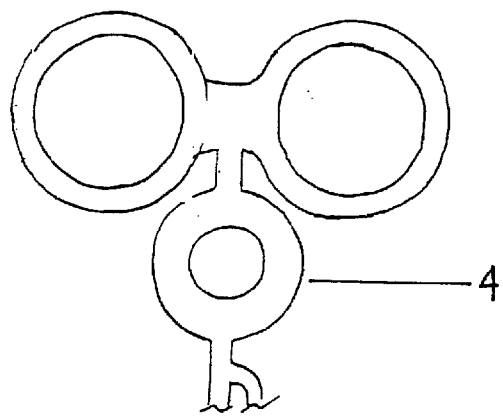
FIG. 16 illustrates an alternate embodiment for the configurations of the coil and two housing sections, where the coil is anterior.
Figure 17:
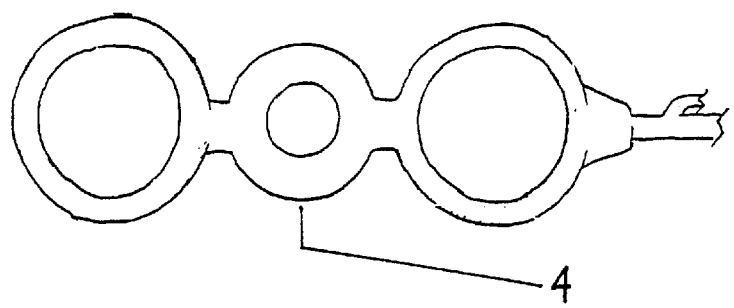
FIG. 17 illustrates an alternate embodiment for the configurations of the coil and two housing sections, where the coil is between the housing sections.
Figure 18:
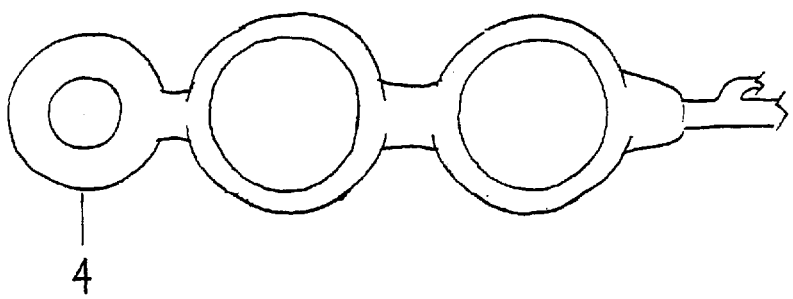
FIG. 18 illustrates an alternate embodiment for the configurations of the coil and two housing sections, where the coil is posterior and all elements are aligned substantially horizontally.

FIG. 14 shows the necessary rotational orientation of the magnets (so as to substantially align the external coil 59 and internal coil 4, one over the other) which orientation can be conveniently accomplished by having two opposing pairs of magnetic poles interact as illustrated by the magnetic lines of force 58.

FIGS. 15, 16, 17, and 18 illustrate alternate embodiments for some of the possible configurations for the implanted part of the invention, showing the coil 4 and the two housing sections 2 and 3.

The above descriptions have been intended to illustrate the preferred and alternative embodiments of the invention. It will be appreciated that modifications and adaptations to such embodiments may be practiced without departing from the scope of the invention, such scope being most properly defined by reference to this specification as a whole and to the following claims.

What is claimed is:

1. A totally implantable cochlear prosthesis comprising a piezoelectric actuator for controlling volume or on/off functions, said actuator being adapted for transcutaneous actuation and further comprising:

at least one hermetically sealed housing section containing various electronics, electrical interconnections, electrical power storage means and said piezoelectric actuator for transcutaneous actuation;

a coil for receiving, from time to time, power and/or data from an external head-mounted means;

an implanted microphone encapsulated in a biocompatible housing;

an electrode array for insertion into one or more scala within the cochlea; and, at least one cable containing wires connecting said coil, microphone and electrode array to said housing section.

2. A totally implantable cochlear prosthesis comprising a piezoelectric actuator for controlling volume or on/off functions, said actuator being adapted for transcutaneous actuation wherein said piezoelectric actuator comprises a snap dome.

3. An implantable cochlear prosthesis comprising at least two thin housings operatively connected to one another wherein said housings are operatively connected to one another by a pliable connector adapted to allow the sections to be bent relative to one another so as to fit the curvature of the skull and to adapt to changes in skull size over time.

4. A prosthesis as in claim 1 wherein said connector comprises gold and/or platinum.

5. A prosthesis as in claim 2 wherein gold and/or platinum foil is used as a cover over said snap dome, such foil being both biocompatible and pliable, so as to provide a means for activating said snap dome, and thus the piezoactuator, by pushing against the outside skin overlaying said foil.

6. A prosthesis as in claim 2 wherein said snap dome comprises air or gas, such air or gas being adapted to be slightly pressurized so as to allow said snap dome to readily "snap" when pushed at a specified force.

7. A totally implantable cochlear prosthesis comprising a piezoelectric actuator for controlling volume or on/off functions, said actuator being adapted for transcutaneous actuation wherein the piezoelectric actuator is made from a piezoceramic, a piezocrystal, or a PVDF (or PVDF copolymer) piezo film.

8. A prosthesis as in claim 1 wherein said cable is comprised of a polymer film containing lithographically formed wires.

9. A prosthesis as in claim 1 wherein the portion of the cable connecting said coil, microphone and electrode array to the housing section(s) is substantially corrugated.

10. A prosthesis as in claim 9 wherein said cable is also longitudinally folded or pleated at least once so as to minimize the width of said connector line.

11. A prosthesis as in claim 1 wherein the electrical power storage means is a secondary or rechargeable battery.

12. A prosthesis as in claim 1 wherein the electrical power storage means is a capacitor.

13. A prosthesis as in claim 1 wherein the electrical power storage means is a rechargeable thin-film lithium chemistry battery, said battery containing a non-liquid electrolyte.

14. A prosthesis as in claim 1 wherein the housing section is fixed to the skull by suturing to the overlaying skin and/or underlying skull, or by using titanium screws drilled into the skull.

15. A prosthesis as in claim 1 wherein the coil for receiving power and/or data is comprised of one or more turns of wire embedded in a polymer film.

16. A totally implantable cochlear prosthesis comprising a coil and at least one housing containing control electronics, wherein said coil is located outside said housing but is operatively connected to said housing wherein said coil contains embedded markings comprised of gold and/or platinum, said markings being coded for post-operative identification of the implanted prosthesis.

17. A prosthesis as in claim 1 wherein the housing section or parts connected to said section contains embedded markings comprised of gold and/or platinum, said being markings coded for post-operative identification of the implanted prosthesis.

18. A cochlear prosthesis system comprising a prosthesis as in claim 1 and said external head mounted means, said external head mounted means comprising a coil to inductively couple electrical power and/or data to said receiving coil.

19. A cochlear prosthesis system comprising a prosthesis as in claim 1 and said external head mounted means, said external head mounted means comprising a battery, electronics and said coil of said external head mounted means mounted onto that part of standard eyeglass frames held by the pinna, said coil being substantially positioned to overlay the receiving coil when said frames are worn, and for inductively coupling electrical power and/or data to the implanted receiving coil.

20. A system as in claim 19 wherein said coil of said head mounted means is connected via wires to a body-worn unit, said unit containing electronics and a power source, said power source being a primary or secondary battery, or an AC wall plug source.

21. A system as in claim 19 wherein said coil of said head mounted means is connected via wires to a programming unit or computer used to set or adjust the implanted electronics from time to time so as to optimize the user's speech percepts.

22. A cochlear prosthesis system comprising a prosthesis as in claim 1 and said external head mounted means, said external head mounted means comprising a battery, electronics and an external coil mounted onto a behind-the-ear type support structure, said structure held by the pinna, where said external coil is substantially positioned for overlay over the implanted coil when said structure is worn, and said external coil inductively coupling electrical power to the implanted coil.

23. A system as in claim 22 wherein said external head mounted means comprises an external coil mounted onto a behind-the-ear type support structure, held by the pinna, said external coil substantially positioned for overlay over the implanted coil when said structure is worn and for inductively coupling electrical power to the implanted coil, said external coil being connected via wires to a body-worn unit, said unit containing electronics and a power source, said power source being a primary or secondary battery, or an AC wall plug source.

24. A system as in claim, 22 wherein said head mounted means comprises an external coil mounted onto a behind-the-ear type support structure, held by the pinna, said external coil substantially positioned for overlay over the implanted coil when said structure is worn, and for inductively coupling data to/from the implanted coil, said coil being connected via wires to a programming unit, such as a computer, said programming unit used to set or adjust the implanted electronics from time to time so as to optimize the user's speech percepts.

25. A totally implantable cochlear prosthesis comprising:
at least one hermetically sealed housing section containing various electronics, electrical interconnections, two magnets, electrical power storage means, means for adjusting volume and/or controlling panic "off/on" functions;
a coil for receiving, from time to time, power and/or data from an external head-mounted means;
an implanted microphone encapsulated in a biocompatible housing;
an electrode array for insertion into one or more scala within the cochlea; and,
at least one cable containing wires connecting said coil, microphone and electrode array to said housing section.

26. A cochlear prosthesis system comprising a prosthesis as in claim 1 and said external head mounted means, said external head mounted means comprising a device containing two magnets, a battery, electronics and an external coil, said device held to the head by two opposing magnets within the implanted housing, said external coil substantially positioned to overlay the implanted coil when the device is used, and said external coil inductively coupling electrical power to the implanted coil and wherein said two magnets in the head mounted means have opposite magnetic polarities, one to the other, and the two magnets in the implanted housing section have opposite magnetic polarities, one to the other, such magnetic arrangement creating, upon the two pairs of magnets interacting, a unique rotational alignment between the external and implanted coils, said arrangement substantially aligning the external coil and implanted coils one over the other.

27. A totally implantable cochlear prosthesis comprising:
at least one hermetically sealed housing section containing various electronics, electrical interconnections, electrical power storage means, means for adjusting volume and/or controlling panic "off/on" functions;
an emergency turn "off/on" switch for controlling electrical power to the electrodes using a magnetic sensor contained within a housing section;
a coil for receiving, from time to time, power and/or data from an external head-mounted means;
an implanted microphone encapsulated in a biocompatible housing;
an electrode array for insertion into one or more scala within the cochlea; and,
at least one cable containing wires connecting said coil, microphone and electrode array to said housing section.

28. A prosthesis as in claim 27 comprising a reed switch, such switch activated by holding a magnet near or against the skin in the vicinity of the implanted reed switch.

* * * * *